(12) United States Patent
Pereira

(10) Patent No.: US 11,703,132 B2
(45) Date of Patent: Jul. 18, 2023

(54) ZERO DEAD LEG VALVE

(71) Applicant: EMD MILLIPORE CORPORATION, Burlington, MA (US)

(72) Inventor: Brian Pereira, Woburn, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 17/438,244

(22) PCT Filed: Jun. 17, 2020

(86) PCT No.: PCT/US2020/038164
§ 371 (c)(1),
(2) Date: Sep. 10, 2021

(87) PCT Pub. No.: WO2020/257300
PCT Pub. Date: Dec. 24, 2020

(65) Prior Publication Data
US 2022/0186841 A1 Jun. 16, 2022

Related U.S. Application Data

(60) Provisional application No. 62/864,648, filed on Jun. 21, 2019.

(51) Int. Cl.
*F16K 3/26* (2006.01)
*F16K 27/04* (2006.01)
(52) U.S. Cl.
CPC .............. *F16K 3/26* (2013.01); *F16K 27/041* (2013.01)
(58) Field of Classification Search
CPC ................................. F16K 3/26; F16K 27/041
See application file for complete search history.

(56) References Cited

U.S. PATENT DOCUMENTS 5,794,659 A * 8/1998 DuRoss .................... F17D 1/04
137/883
8,690,120 B2 4/2014 Hartnett et al.
(Continued)

FOREIGN PATENT DOCUMENTS

DE 20318927 U1 6/2004
EP 2286870 A1 2/2011
(Continued)

OTHER PUBLICATIONS

First Examination Report received for Indian Application No. 202117045414 dated Mar. 14, 2022, 6 pages.
(Continued)

*Primary Examiner* — Kevin R Barss
(74) *Attorney, Agent, or Firm* — EMD Millipore Corporation

(57) ABSTRACT

A valve having a body having a first section and a second section; an extended flange attached to the second section of the body or disposed as an integral part of the second section of the body; an elongate bore extending through the body and having a proximal end and a distal end; a longitudinally displaceable plunger disposed in and extending along the bore, the plunger having a proximal end and a distal end and having a first position displaced toward the distal end of the bore and a second position displaced toward the proximal end of the bore; a diaphragm seal attached to the proximal end of the plunger and sealing the bore at the proximal end thereof; a gland seal sealing the bore at a location intermediate the diaphragm seal and the distal end of the bore; the plunger extending through and being sealingly secured to the gland seal; a fluid transfer opening in the bore between the diaphragm seal and the gland seal; longitudinal displacement of the plunger moving the diaphragm seal to open the bore, the gland seal stretching to accommodate the displacement of and maintain a seal about the plunger, a fluid flow (Continued)

path being established between the open proximal end of the bore and the fluid transfer opening, wherein longitudinal displacement of the plunger towards its first position moves the diaphragm to open the bore. The valve further comprises an extended flange having a surface that is approximately coplanar with a surface of the second position when the plunger is displaced toward the proximal end of the bore, creating a zero dead leg position.

27 Claims, 14 Drawing Sheets

(56) References Cited

U.S. PATENT DOCUMENTS

| | | | |
|---|---|---|---|
| 9,074,692 B2 * | 7/2015 | Equit | F16K 27/0236 |
| 9,090,398 B2 | 7/2015 | Hobson et al. | |
| 9,187,240 B2 | 11/2015 | Hobson et al. | |
| 9,272,840 B2 | 3/2016 | Hobson et al. | |
| 10,247,312 B2 | 4/2019 | Hartnett et al. | |
| 2009/0069791 A1 | 3/2009 | Connolly et al. | |
| 2012/0260608 A1 | 10/2012 | Pethe et al. | |
| 2016/0208927 A1 | 7/2016 | Hartnett et al. | |

FOREIGN PATENT DOCUMENTS

| | | |
|---|---|---|
| EP | 3446020 A2 | 2/2019 |
| JP | 2009-120402 A | 6/2009 |
| WO | 2017/182814 A2 | 10/2017 |

OTHER PUBLICATIONS

International Search Report received for PCT Patent Application No. PCT/US2020/038164, dated Nov. 8, 2020, 5 pages.
Office Action received for Canadian Patent Application No. 3,137,122 dated Jan. 6, 2023, 3 Pages.
Office Action received for Japanese Patent Application No. 2021-566197 dated Mar. 7, 2023, 5 Pages (3 Page of English translation and 2 pages of official copy).

* cited by examiner

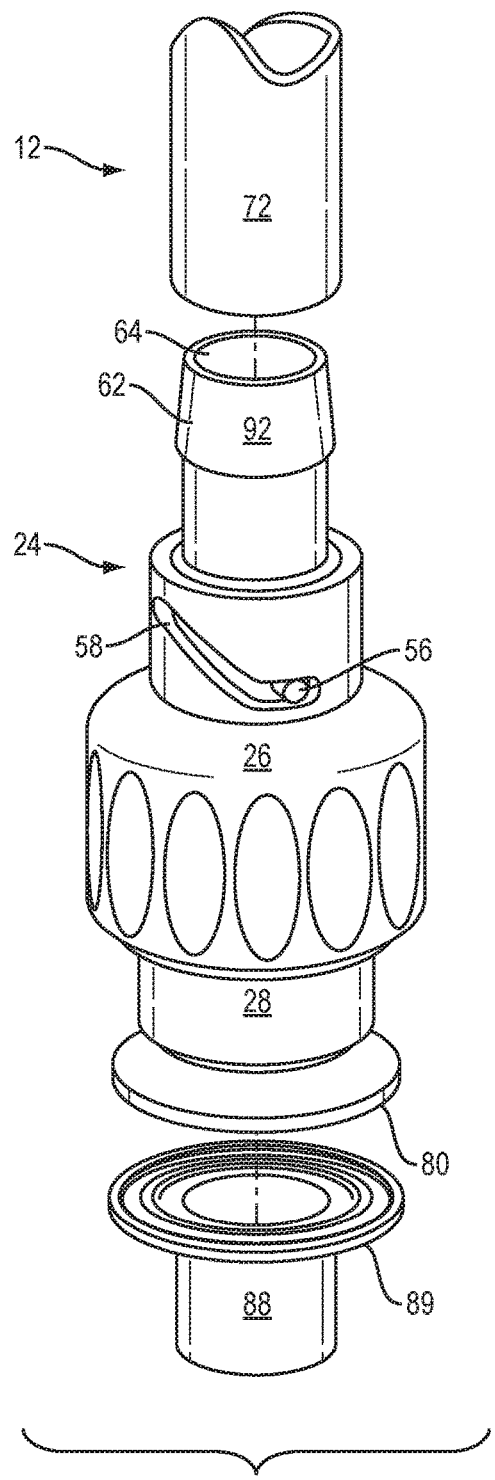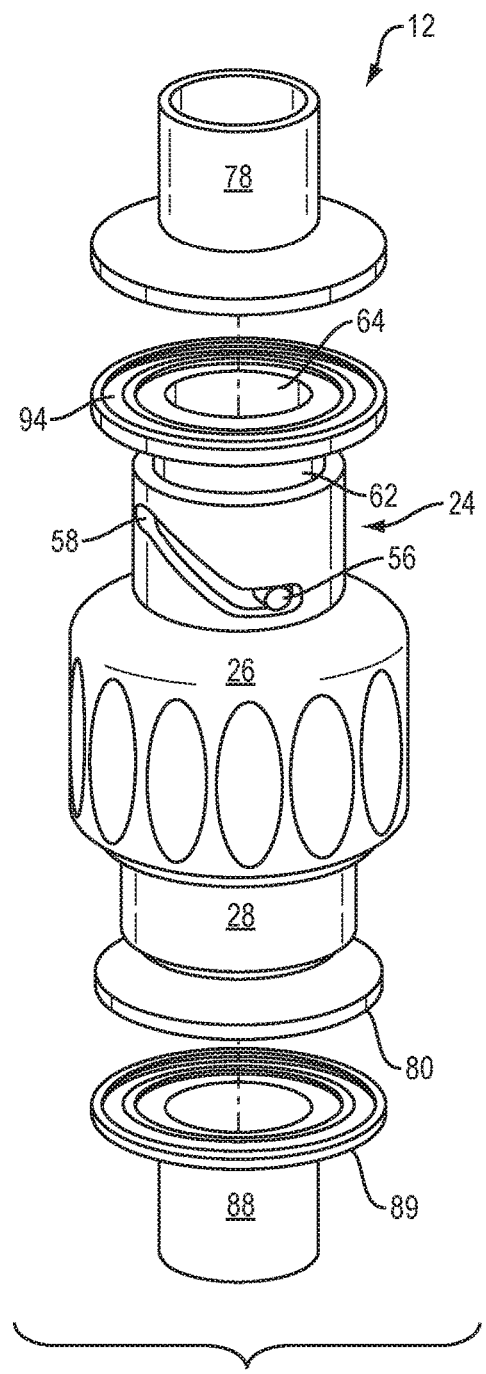
FIG. 2A
FIG. 2B

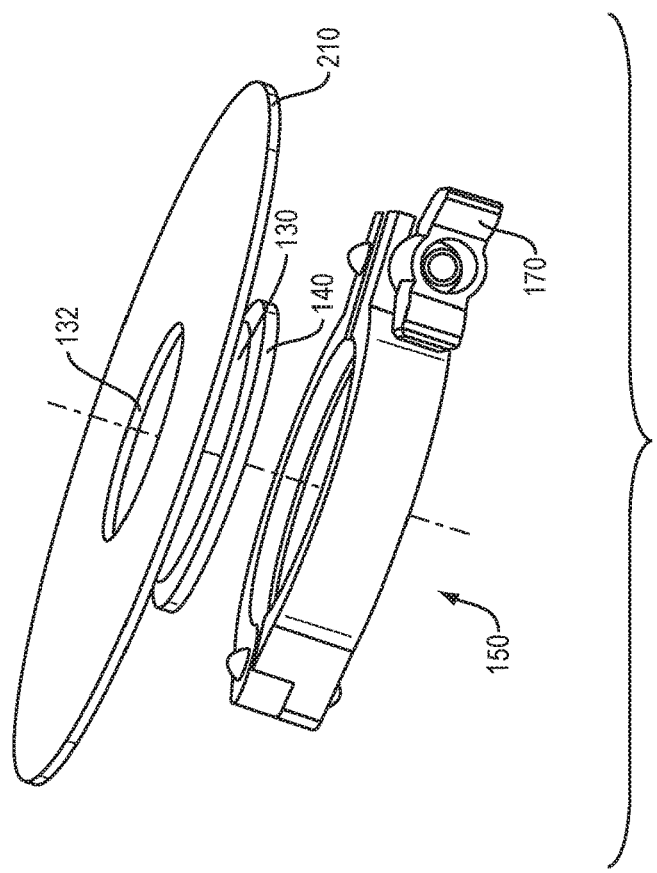
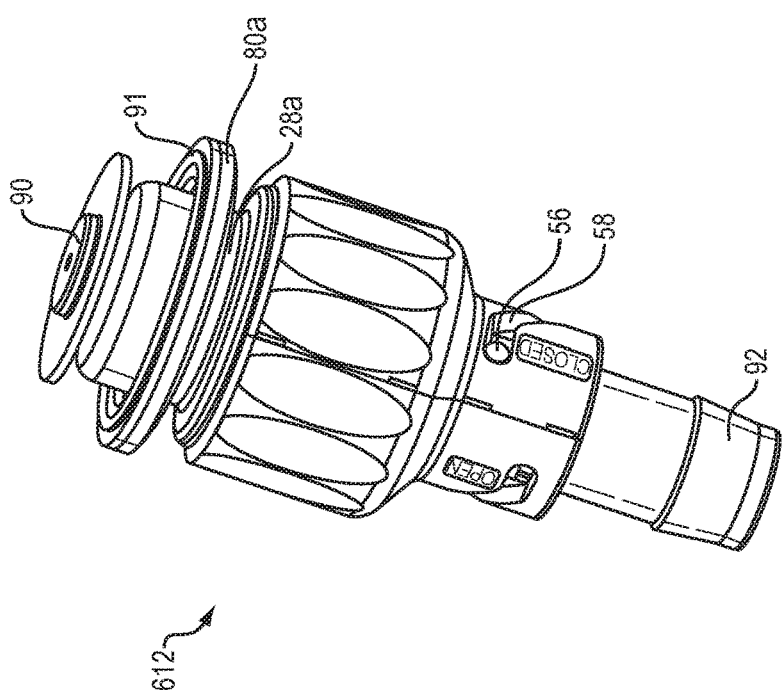

ZERO DEAD LEG VALVE

RELATED APPLICATIONS

This application is a U.S. National Stage application of International Application No. PCT/US2020/038164, filed Jun. 17, 2020, which claims the benefit of priority to U.S. Provisional 62/864,648, dated Jun. 21, 2019, each of which is incorporated by reference in its entirety.

BACKGROUND

Field of the Disclosure

Embodiments of the present disclosure relate to containers useful as mixers or bioreactors. More particularly, embodiments disclosed herein include a valve in fluid communication with an inner volume of the containers.

Description of the Related Art

Traditionally, biological fluids have been processed in systems that use stainless steel containers. These containers are sterilized after use so that they can be reused. The sterilization procedures are expensive and cumbersome and often ineffectual at times. More recently, containers have comprised flexible containers, such as flexible containers manufactured from flexible polymeric films. To provide greater flexibility in manufacturing and reduce times needed to sterilize and regenerate the equipment, manufacturers employ single use sterilized containers, such as bags, e.g., two-dimensional (pillow-shaped) or three-dimensional bags. Such bags are used once for processing a biological product, whether in batch, semi-continuous, or continuous mode, and are subsequently discarded. These single use bags consist of a system for mixing two or more ingredients, at least one of which is liquid and the other(s) being liquid or solid, wherein the bag has a mixing element or the like for causing the contents to mix as uniformly as possible.

It is often favorable to supply materials and/or processing aids, e.g., antifoam agents, nutrients, and the like to the system for cell growth in a bioreactor or for other purposes in a bag or mixer during processing. Typically, these materials are added either via a plurality of ports in the top and bottom of the container or bag, wherein the mixing element distributes them. However, this is an inefficient method for distribution in that the port is typically located along an inner surface of the container and distribution of the materials to where they are needed is often incomplete. For example, ports are located at the bottom or a sidewall of a container and have a tube attached thereto. The tube may become filled with a fluid having a different concentration, i.e., weaker or stronger, of components than the concentration of the fluid remaining in the container, making a product sample taken thereof less accurate and potentially misleading. Similarly, in the case where aids and agents settle, irrespective of whether introduced into the container from a top, bottom, or sidewall, before dissolving, near the port or within the tube (i.e., "dead-leg"), those aids and agents are not available later for mixing within the fluid, wasting valuable reagents. In the past, such waste was only avoided by very slowly introducing reagents into the container or by using very high, but unfavorable, mixing speeds, which impart shear stresses. Also, samples are often taken from the ports or tubing having a dead-leg, which is often of a differing concentration and/or requires a significant amount of biological fluid to be withdrawn, which is wasteful. Manufacturers may use dip tubes to take samples from containers but must also be sterilized and may contaminate the fluids within the container. Accordingly, the use of dip tubes is disfavored.

Good mixing of agents, aids, and components helps to optimize bioreactor processes. The production of vaccines, the liquids and biological components, often require the addition of soluble, solid processing agents. For example, aluminum salt is used as an adjuvant, which improves the efficacy of the vaccine by enhancing the body's immune response. Unfortunately, the adjuvants often consist of particle sizes larger than 0.2 microns and are prone to settling at the bottom of the container, which are subsequently not dissolved or mixed into solution.

A well-designed mixing system provides three basic functions: creation of constant conditions (nutrients, pH, temperature, etc.) in a homogeneous distribution; dispersion of gas for supplying, e.g., oxygen, and extracting carbon dioxide where and when needed as in a bioreactor or container; and/or optimization of heat transfer. Providing acceptable mixing, without imparting damaging shear effects, becomes more challenging as the size and/or aspect ratio of the bioreactor container increases. Certain commercial mixer and bioreactor platforms include a single bottom mounted impeller. Single bottom impellers produce a vortex having stagnant zones, decreasing mixing. Multiple impellers and/or higher impeller speeds improve overall mixing and mixing speeds. However, higher shear rates associated with multiple impellers and/or high impeller speeds, as well as some baffles, can damage cells within the container.

Some bags, bioreactors, or containers, whether rigid or flexible, include a baffle formed vertically along at least a portion of an inner sidewall of the bag for improved mixing. These baffles are typically sleeves and often have a rigid member such as wood, plastic, or metal shaped to fit into the interior of the sleeves, which can damage the container. Large volume bags, e.g., 1000 L to 3000 L volume bags, containers, or bioreactors, in particular, present challenges for mixing components uniformly, because as the increased height of these systems, despite the reduced height to width aspect ratios, mixing efficiency decreases.

It is an advance in the art to provide a valve for use with containers for the mixing of biological fluids that promotes homogeneous mixing and sampling. Also, it is an advance in the art to provide a single use valve for use with containers for the mixing of biological fluids that promotes homogeneous mixing and sampling. It is a further advance to provide a valve in which there is zero dead-leg within a process, such that concentrations of components, agents, aids, etc., within a solution or a fluid are consistent.

SUMMARY

A fluid transfer device, such as a valve, comprising a body having a first section and a second section; an extended flange attached to the second section of the body or disposed as an integral part of the second section of the body; an elongate passage or bore extending through the body and having a proximal end and a distal end; a longitudinally displaceable plunger disposed in and extending along the bore, the plunger having a proximal end and a distal end and having a first position displaced toward the distal end of the bore and a second position displaced toward the proximal end of the bore; a diaphragm seal attached to the proximal end of the plunger and sealing the bore at the proximal end thereof; a gland seal sealing the bore at a location intermediate the diaphragm seal and the distal end of the bore; the plunger extending through and being sealingly secured to the gland seal; a fluid transfer opening in the bore between the diaphragm seal and the gland seal; longitudinal displacement of the plunger moving the diaphragm seal to open the bore, the gland seal stretching to accommodate the displacement of and maintain a seal about the plunger, a fluid flow path being established between the open proximal end of the bore and the fluid transfer opening, wherein longitudinal displacement of the plunger towards its first position moves the diaphragm to open the bore. The fluid transfer device or valve, optionally, further comprises an extended flange having a surface that is approximately coplanar with a surface of the second position when the plunger is displaced toward the proximal end of the passage or bore, creating a zero dead leg condition, substantially as shown in and/or described in connection with at feast one of the figures, as set forth more completely in the claims. Various benefits, aspects, novel and inventive features of the present disclosure, as well as details of exemplary embodiments thereof, will be more fully understood from the following description and drawings.

Embodiments of the disclosure include a valve in fluid communication with a container, such as a bag, bioreactor, and or the like, for a fluid, comprising an inner volume formed of a flexible material, optionally, one or more inlets in said container, optionally, one or more outlets in said container, an impeller assembly mounted at least partially within said volume of said container, and a baffle in said inner volume of said container. In some embodiments, an extended flange may be attached to the valve and the bag or bioreactor. In some embodiments, the extended flange may be attached to the valve via a clamp. In some embodiments, the valve may have an extended flange integrally formed therewith for attaching to a bag or bioreactor. The flange is adhered to the bag or bioreactor or container, for example, using an adhesive or by heat-sealing. The bag or bioreactor may be a two-dimensional bag or a three-dimensional bag as is known to those in the art.

Embodiments according to the disclosure also include methods for processing and/or sampling biological fluids. A biological fluid(s) can be delivered or otherwise provided within a bag or bioreactor having an inner volume. A fluid transfer device, such as a valve, is located downstream and in fluid communication with the bag or bioreactor. The flange may comprise a relatively large surface for attachment to the bag or bioreactor. The valve is attached to the bag or bioreactor along an extended area of a flange that is attached to or an integral part of the valve. The biological fluids are mixed using, e.g., an impeller and/or mixing blade. The impeller may be attached to a physical shaft as a drive mechanism or may be powered by a magnetic drive pump, using a balanced magnetic field to create the rotation of the impeller. A solid processing agent(s) may be delivered to the inner volume of the bag or bioreactor for mixing with the biological fluids. Also, the valve may comprise a plunger for providing a fluid tight seal when in a closed position and for allowing delivery of fluids when in an open position. In some embodiments, the flange comprises a top surface that is substantially coplanar with a surface of the plunger during a closed position. In some embodiments, the surface of the plunger is higher than a top surface of the flange. Because the flange is adhered to the bag or bioreactor, the mixing is performed absent a dead-leg region, vastly increasing mixing efficiency. Furthermore, sampling during the processing of fluids will also be more representative of concentrations of cell cultures, viruses, various agents and/or aids.

Embodiments of the valve(s) having an extended flange according to the disclosure described herein facilitate the mixing of various processing agents or aids, e.g., adjuvants, cell culture media, nutrition additives, antifoaming agents, and/or the like.

BRIEF DESCRIPTION OF THE FIGURES

FIGS. 2A and 2B are exploded, perspective views of embodiments according to the disclosure, further comprising alternative embodiments of upstream and downstream attachment components;

FIGS. 4A and 4B are perspective views of embodiments, further comprising a detachable extended flange and a clamp, according to embodiments of the disclosure;

DETAILED DESCRIPTION OF SOME EMBODIMENTS

Figure 1A:
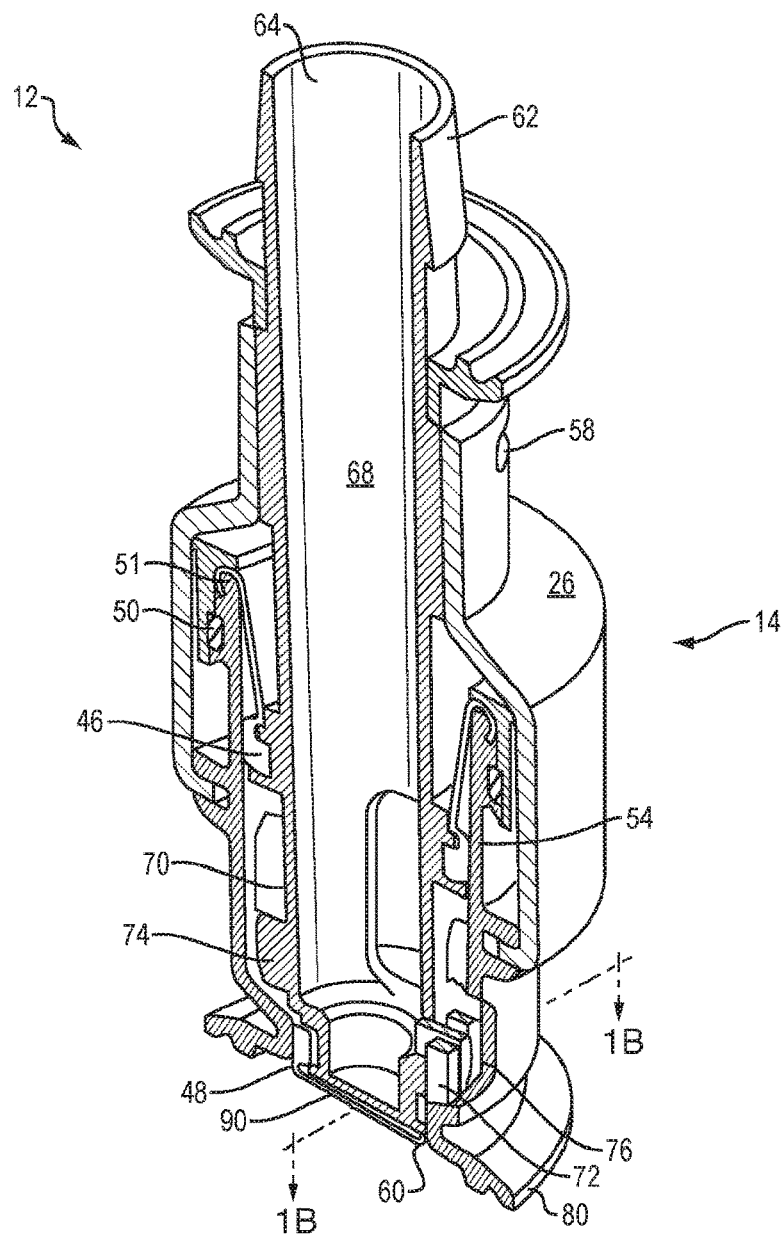
FIGS. 1A and 1B are cross-sectional views of an embodiment of a valve according to the disclosure in a closed position.

So the manner in which the features disclosed herein can be understood in detail, a more particular description of the embodiments of the disclosure, briefly summarized above, may be had by reference to the appended drawings. It is to be noted, however, that the appended drawings illustrate only typical embodiments of this disclosure and are therefore not to be considered limiting of its scope, for the embodiments described and shown may admit to other equally effective embodiments. It is also to be understood that elements and features of one embodiment may be found in other embodiments without further recitation and that identical reference numerals are sometimes used to indicate comparable elements that are common to the figures.

The term "dead-leg" within this disclosure is defined as an area within a conduit, tube, or channel, typically leading to an outlet, which sees less fluid flow or turbidity than within a larger volume of a container in fluid communication therewith, although the dead leg area is not necessarily insulated from flow.

The term "valve" within this disclosure is generally defined as a mechanical or electrical, or electro-mechanical device capable of controlling the passage of a fluid, i.e., fluid flow, through a channel or bore through the device.

The terms "bioreactor," "bag," and "container" are generally used interchangeably within this disclosure. A flexible bioreactor, bag, or container connotes a flexible vessel that can be folded, collapsed, and expanded and/or the like, capable of containing, for example, a biological fluid. A single use bioreactor, bag, or container, typically also flexible, is a vessel that is used once and discarded.

The term "sterile" is defined as a condition of being free from contaminants and, particularly within the bioprocessing industry, free from viruses, bacteria, germs, and other microorganisms.

The term "adjuvant" within this disclosure is defined as a substance that enhances a body's immune response to, for e.g., an antigen.

The term "upstream" is defined as the condition of being in a position prior to another component with respect to the direction of the flow of a fluid.

In general, embodiments according to the disclosure describe sterile fluid transfer devices, such as a flow-through connector or valve, for transporting fluids, e.g., fluids, solutions, liquids and/or gases. In some embodiments, the fluid transfer device has a body, a bore located in an interior region of the body, and a movable (linearly, e.g., push pull manipulation, and/or rotationally, e.g., a torque applied to the body for opening and closing the bore) plunger contained within the bore. The body is formed from a first and a second section. The first section has a first end containing a first opening and a termination attachment component, such as a flange or the like surrounding the first opening for attaching the body to an upstream component(s). The second section has a second end containing a second opening, wherein the bore connects the first and second openings. The first section may, optionally, rotate with respect to a portion of the second section. In some embodiments, the first section and a portion of the second section telescope in a push-pull manner.

The movable plunger includes a first end containing a first opening, a second end containing a second opening, a fluid channel located in the interior of the plunger connecting the first and second openings of the plunger. In some embodiments, the movable plunger rotates and moves in a linear or axial manner. In some embodiments, the plunger includes a component for inhibiting its rotation, while promoting its linear or axial movement within the bore during rotation of the first section of the body when the device is operated (i.e., opened/closed). In some embodiments, the plunger includes a component for inhibiting its linear travel, while promoting its linear or axial movement within the bore during telescoping of the first section of the body when the device is operated or manipulated (i.e., opened/closed).

The fluid transfer device, a valve, is in the closed position when the first end of the plunger is in alignment with, e.g., an attachment component surrounding the first opening of the body, wherein a fluid resistant seal is formed. In some embodiments, the surface of the plunger is higher than a top surface of the flange. A steam-able face for sterilization purposes is also formed, wherein the flange is comprised of a steam-able plastic, e.g., polypropylene, acetal, nylon, and others. The device is in the opened position when the first end of the plunger is not in alignment with the attachment component surrounding the first opening of the body, wherein fluids are permitted to enter the device from an upstream component, for example, a bag, bioreactor or biocontainer.

Figure 1B:
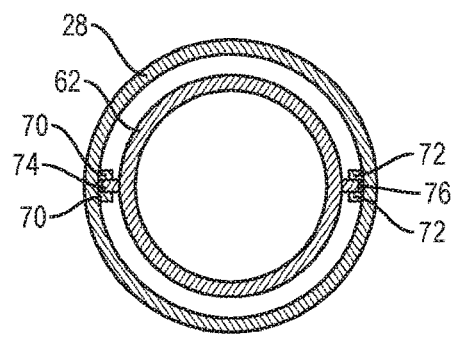
Figure 1C:
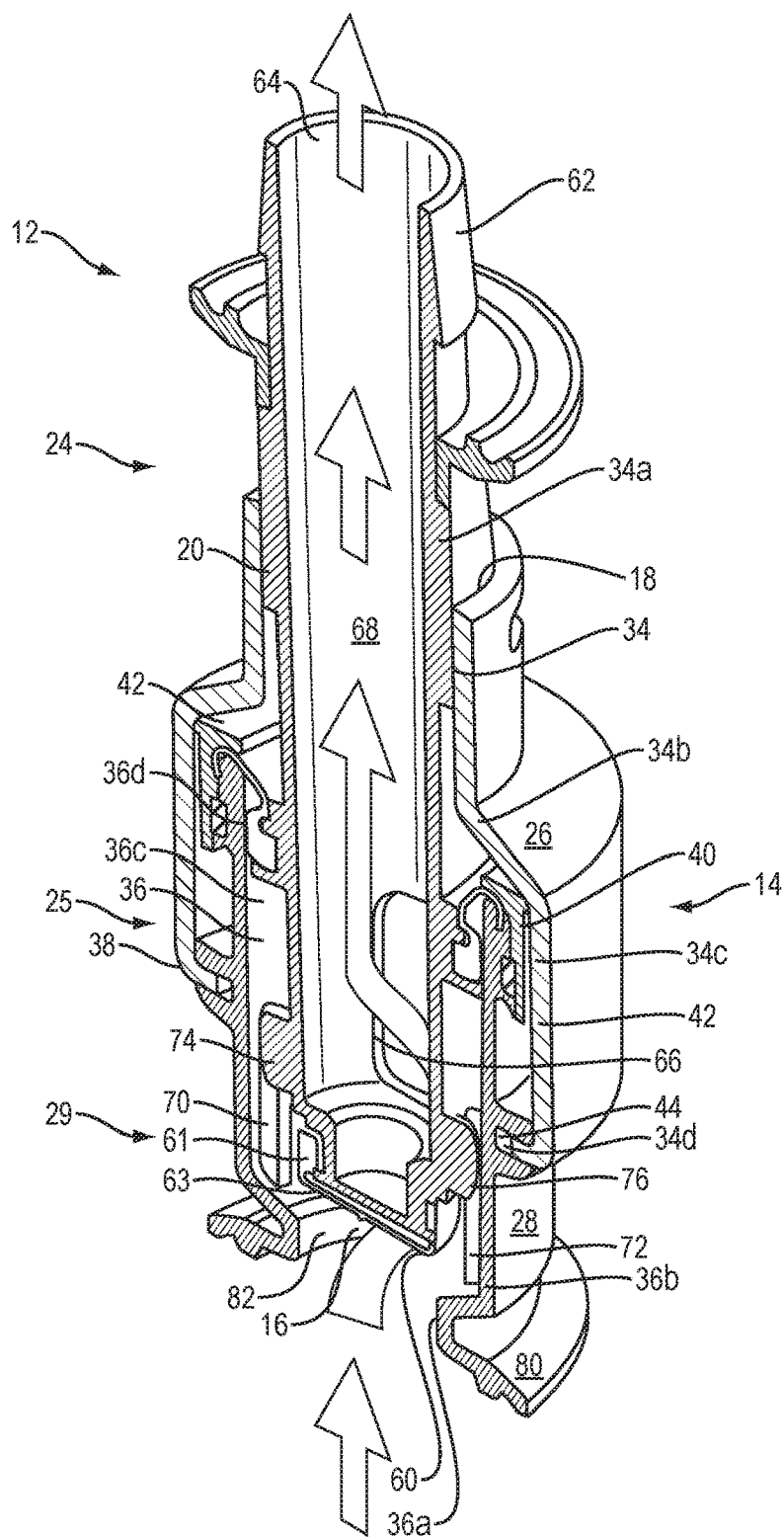
FIG. 1C is a cross sectional view of the embodiment of the valve of FIGS. 1A and 1B having the plunger in an opened position.

Turning to the figures, FIGS. 1A and 1B are cross-sectional views of an embodiment according to the disclosure in a closed position. Some embodiments of the disclosure are shown in FIGS. 1A, 1B, and 1C, which include a fluid transfer device, e.g., a valve 12 having a body 14 having an elongate bore 20 formed through at least a portion of the interior of the body 14, and a generally hollow moveable plunger 62, i.e., a longitudinally displaced plunger, contained within the bore 20. The bore 20, as shown in FIG. 1C, is a lateral central bore formed through an interior length of the body 14. The body 14, as shown, is formed from two sections, a rotating first section 26 and a stationary second section 28. The first section 26 rotates partially around a portion of the stationary second section 28 and plunger 62. A bore section 34 generally cooperates with the inner wall of rotating first section 26, and a bore section 36, which generally corresponds to the inner wall of stationary second section 28. In the embodiment depicted in FIG. 1C, each of the bore sections (34, 36) has a different diameter. As will be described in greater detail herein, the valve 12 is operated (i.e., opened/closed) when the first section 26 of the body 14 is rotated, engaging the stationary second section 28 of the body 14 and the plunger 62, driving the plunger 62 linearly (e.g., axially) within the bore 20, thereby operating (i.e., opening and closing) the valve 12.

FIG. 1C is a cross sectional view of the embodiment of the valve 12 of FIGS. 1A and 1B having the plunger in an opened position. As shown in FIG. 1C, the first section 26 of the body 14 is generally hollow and has an opening 18 at one end for receiving the plunger 62. The first section 26 includes a protruding lip or edge component 38 that is rotatably engaged by a stationary wall receiving groove 44 on the outer stationary 28 wall section. The stationary second section 28 of the body 14 is generally hollow and has an opening 16 at one end that permits a fluid provided from an upstream source (not shown) to pass through it during an open position. The opening 16 also receives the bottom 63 of the plunger when the valve 12 is closed. The stationary section 28 includes an outer wall component 42 for rotatably engaging the inner wall section 40 of the rotating section 26. As shown in FIG. 1C, the inner wall of the second section 28 forms the stationary bore section 36 having four sections. In FIG. 1C, a first stationary bore diameter 36a, a first transition stationary bore section 36b, a second stationary bore diameter 36c, and a second transition stationary bore section 36d are depicted. The first bore diameter 36a is less than the second bore diameter 36c. The second bore diameter 36c is a set diameter. The first transition bore section 36b is arranged between the first and second bore diameters (36a, 36c) and has an outwardly tapering diameter along its length. The diameter of the first transition section 36b is, in some embodiments, a linear outward progression between the first and second bore diameters (36a, 36c). The diameter of the first transition section 36b adjacent the first diameter 36a is equal to the diameter 36a, and the diameter of the first transition section 36b adjacent the second diameter 36b is equal to the diameter 36b.

As shown in FIG. 1C, the plunger 62 has three general regions comprising a first, second and third region. The first region 24 has a diameter equal to or less than a first bore set diameter 34a. The second region 25 has a diameter equal to or less than a second stationary bore diameter 36c. The third region 29 has a diameter equal to or less than that of the first stationary bore diameter section 36a. The plunger 62 has a bottom component 63 at the end of the third region 29 for blocking the opening 16 of the stationary section 28 when the device is in the closed position, as shown in FIG. 1A. Some embodiments of the disclosure, as depicted in FIG. 1C, include a static diaphragm seal 60 located on the bottom 63 of the plunger 62 forming a tight fluid resistant seal between the outer wall 61 of the bottom end 63 of the plunger, and the inner wall 82 of the stationary section 28 of the body forming the opening 16.

The plunger 62 also comprises two openings, a first opening 64 and a second opening 66. A channel 68 is located within the interior of the plunger and connects the first and second openings (64, 66), thereby forming a fluid pathway to a downstream component. As shown in FIG. 1C, the first opening 64 is located in the first portion 24 of the plunger, and the second opening 66 is located in the second portion 25 of the plunger. In other embodiments, plunger 62 can contain additional openings and interior fluid pathways. In some exemplary embodiments, the plunger 62 contains at least openings in the second portion 25 (not shown).

Some embodiments of the disclosure, as depicted in FIGS. 1A-1C, include wherein the plunger 62 comprises a component for inhibiting the rotation of the plunger 62 within the bore 20, while promoting linear movement of the plunger 62 when the valve 12 is operated (i.e., opened/closed). Some embodiments for accomplishing the linear movement of the plunger 62, as shown in FIG. 1A, depicts the plunger having a pair of wings (74, 76), fins, or the like, that extend from the outer wall of the plunger 62 towards the inner wall of the second section 28 of the body 14. The second section 28 has a component for interacting with the pair of wings (74, 76) comprising two corresponding pairs of parallel slots (70, 72), grooves, or the like located on the inner wall of the section 28 for receiving the pair of wings (74, 76) in order to restrict the rotation of the plunger 62 and promote the linear movement of the plunger 62 within the bore 20. The pair of wings (74, 76) ride between each corresponding pair of the slots (70, 72) thereby facilitating the linear movement of the plunger 62 within the bore 20 during operation (opening/closing) of the valve 12.

In FIG. 1C, when the valve 12 is in the closed position the bottom end 63 of the plunger 62 is in alignment with a first flange 80, forming a face 90. The valve 12 having the face 90 is a steam-able surface and provides a sterile barrier against the environment for the interior of the device 12, the plunger 62 and any downstream components therefrom. In the closed position, as in FIG. 1A, the bottom end (not shown) of the plunger 62 does not permit fluid to enter opening 16 (shown in FIG. 1C) in the valve from an upstream component (not shown), thereby preventing any fluid from traveling downstream.

In FIG. 1C, the first section 26 also includes an inner wall having a stationary wall engaging section 40 and forms a bore section 34 having four sections. There is a first bore set diameter 34a, a transition bore section 34b, a second bore diameter 34c and a third bore diameter 34d. The first set diameter 34a engages the plunger as it moves linearly within the bore 20. The transition section 34b is arranged between the first and second diameters (34a, 34c) and has an outwardly tapering diameter along its length. The diameter of the transition section 34b is preferably linear outward progression from the first diameter section 34a, wherein the diameter of the transition section 34b adjacent the first diameter 34a is equal to the first diameter 34a, and the diameter of the transition section 34b adjacent the second diameter 34c is equal to the diameter 34c. In some embodiments, the third diameter 34d is preferably less than diameter 34c and, in some embodiments, greater than the diameter 34a.

FIGS. 2A and 2B are exploded, perspective views of embodiments according to the disclosure, further comprising alternative embodiments of upstream and downstream attachment components. As shown in FIG. 2A, the end of the first plunger region 24 includes, in this embodiment, a barb termination 92 for connecting the device to a downstream component, in this instance, tubing 72. As shown in FIG. 2B, the end of first plunger portion 24 comprises a termination flange 94 for connecting the device 12 to a downstream component, e.g., a termination flange 78. By way of example, and not limitation, the downstream components attached to the device by the termination connection feature on the plunger 62 may include plastic tubing 72 and the like, as shown in FIG. 2A, attached to a plastic bag, container or bioreactor or other type of known receptacle (not shown), and the like. As shown in FIGS. 2A and 2B, the valve 12 has at one end of the stationary section 28 of the body a component for attaching the device to an upstream component. In this embodiment, the first flange 80 attaches to a second flange 89 of an upstream component 88.

By way of example, the upstream component attached to the device can be a pipe, a stainless steel or single use plastic tank having an outlet, and the like, having an attachment flange (as depicted in FIGS. 2A and 2B), or any other mode of attachment for connecting components to transfer devices as are commonly known in the art. For example, the flange 80 on valve 12 can be connected to the second flange 89 of the upstream component 88 or pipe by a clamp such as a Tri-Clover™ fitting/clamp (shown below), Ladish™ fitting, ClickClamp™ clamp and the like.

When using the valve 12 to fill a downstream component such as a bag, or any collection vessel attached the tubing 72, the device is opened by rotating the rotating section 26 of the body, which moves the plunger 62 linearly (see FIG. 1B) away from the face 90, permitting fluid to enter opening 16 (see FIG. 1C) and to eventually flow out the opening exit 64 through tube 72, and into a bag, or any collection vessel or other fluid transport device (not shown). Once a bag or bioreactor is full, the rotating section 26 is rotated in the opposite direction to move the plunger linearly again, this time in the opposite direction, in order to seal the opening 16 closed to the fluid from an upstream component.

One or more seals are arranged along the length and end of the plunger 62 to form a fluid tight seal between various portions of the plunger 62 and the bore 20 when the device is in the closed or opened positions. As shown in FIG. 1A seals 60 and 54 are partly contained within grooves 46 and 48. As shown in FIGS. 1A-1C, the seals may be mounted on the plunger 62. However, if desired, a different configuration of seals and their placements can also be used. For example, FIG. 1A shows seals 46 and 60 formed in grooves on the plunger 62. A linear or gland seal 51 is retained within a groove 50 on the inner wall of the stationary bore section and within a groove 46 on the plunger 62. Other embodiments of the present disclosure are also contemplated, such as molding the valve 12 into a single use plastic container such as a single use process bag for the manufacture and transfer of biotech products and the like. Such bags are available from, e.g., EMD Millipore Corporation, Burlington, Mass., USA.

Figure 3:
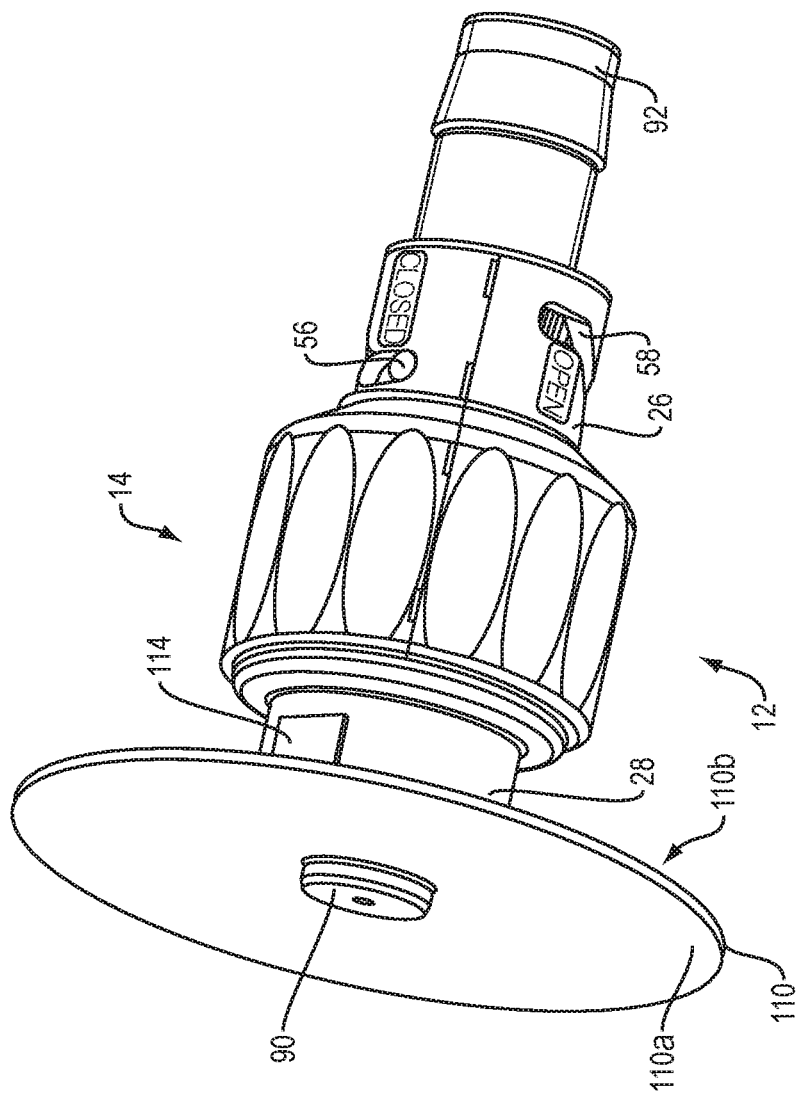
FIG. 3 is a perspective view of a valve having an extended flange, according to embodiments of the disclosure.

FIG. 3 is a perspective view of a valve 12 having an extended flange 110, according to embodiments of the disclosure. The extended flange 110 has a process side 110a and a non-process side 110b opposite that of the process side 110. The extended flange 110 is adhered, such as by heat-sealing, ultrasonic heating, chemical adhesives, etc., to a bag or biocontainer (not shown). In some embodiments, the non-process side 110b of the extended flange 110 is adhered to a bag or biocontainer. The valve 12 comprises a first section 26 and a second section 28. The first section 26 rotates partially around a portion of the second section 28 and the plunger 62. Optionally, the second section 28 further comprises one or more flats 114. A wrench may engage the flat(s) 114, so that the second section 28 does not move during opening and closing of the valve. By restricting the movement of the second station 28, as the first section 26 is rotated top open and close the valve 12, a bag adhered thereto will not be stressed, tear and/or the like. The plunger 62 can contain one or more cams 56 (one shown) that ride in one or more cam slots 58 (one shown) located in a rotating section 26 of the body 14. The arrangement of the cam 56 and slot 58 acts to limit the length the plunger 62 travels linearly within the bore (not shown) when the device is actuated (opened or closed). When the valve 12 is in the closed position, as shown in FIG. 3, the cam 56 sits in the closed position of the cam slot 58. When the valve 12 is in the opened position (not shown), the cam 56 sits in the opened position of the cam slot 58. The extended flange 110 may be integrally formed with the second section 28, i.e., are glued permanently together or are formed together, e.g., in an injection molding operation, such that they cannot be separated without destruction.

FIGS. 4A and 4B are perspective views of embodiments of the disclosure, comprising a valve 612 and further comprising a detachable extended flange 210 and a clamp 150, according to embodiments of the disclosure. The valve 612 comprises a second section 28a and a recessed flange 80a upon which an o-ring 91 is capable of being seated. As shown in FIG. 4B, an extended flange 210 forms a center hole 132 and is disposed adjacent a cylinder 130, and a shoulder 140 having a larger diameter than the cylinder 130. The outside diameter of the shoulder 140 is substantially similar to an outside diameter of the recessed flange 80a. A tri-clamp 150 having a clasp 170 is shown, although many clamps are suitable. When assembled, the extended flange 210 is mated with the valve 612 wherein a surface of the shoulder 140, that is distal to the cylinder 130, contacts the recessed flange 80a. Typically, an o-ring 91 or other compliant sealing means is disposed between the shoulder 140 and the recessed flange 80a. It is to be further understood that the cylinder 130 may also be long enough to incorporate one or more flats (as described above with respect to FIG. 3).

Figure 4C:
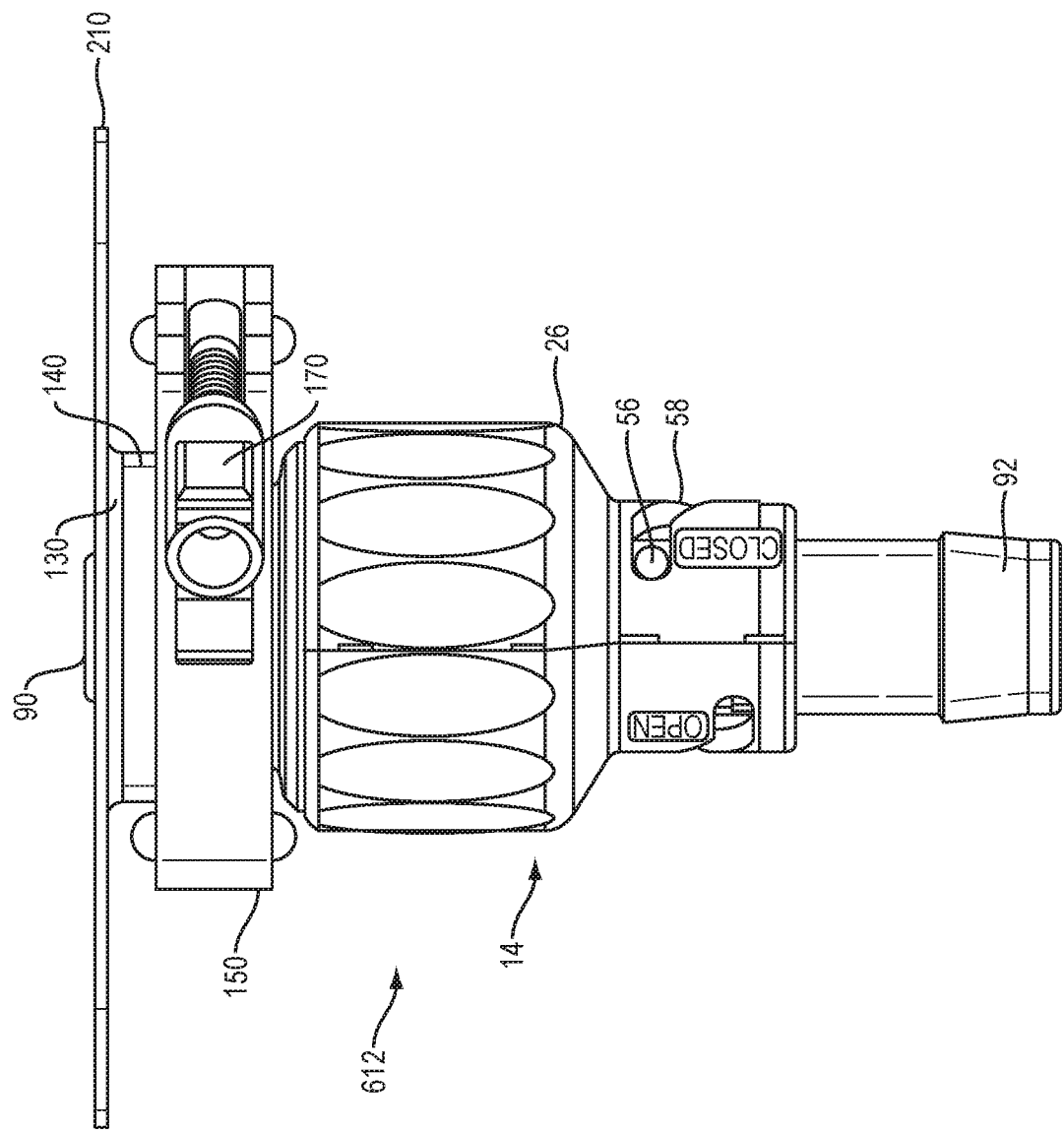
FIG. 4C is a front view of the embodiments of FIGS. 4A and 4B, depicting an extended flange, a valve, and a clamp in an assembled state.

FIG. 4C is a front view of the embodiments of FIGS. 4A and 4B, depicting an extended flange 210, a valve, and a clamp 150 in an assembled state. Once the shoulder 140 and the recessed flange 80a are mated, as described above, the tri-clamp 150 is disposed around both. The clasp 170 may then be tightened, forming a liquid tight seal. In practice, the extended flange 210 may first be adhered to a bag or container (shown below) and subsequently assembled to the recessed flange 80a with the clamp 150. The valve 612 is then in communication with the bag or container. Once the valve 612 is connected, it can be operated. As shown, the valve 612 is in a closed position. To open the valve 612, a user can grip the clamp 150 with one hand and the first section 26 of the body 14. Rotating the body 14, while non-rotating the clamp 150 allows a user to open the valve 612 without compromising the seal between the bag and the extended flange 210.

Figure 5:
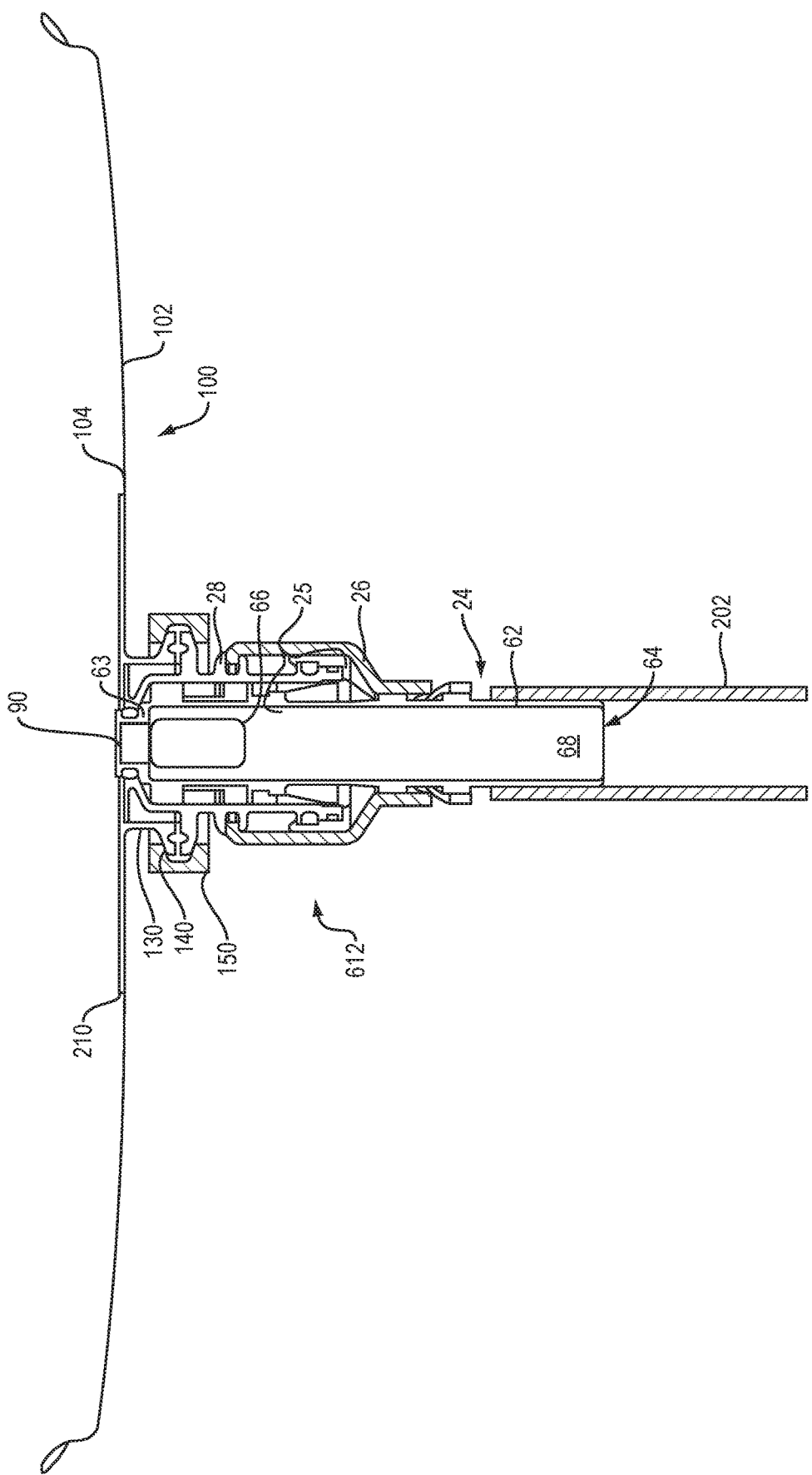
FIG. 5 is a cross-sectional front view of FIG. 4C of a valve having an extended flange adhered to a bag or biocontainer, according to embodiments of the disclosure.

FIG. 5 is a cross-sectional front view of FIG. 4C of a valve 612 having an extended flange 210 adhered to a bag or biocontainer 100, according to embodiments of the disclosure. The valve 612 operates like the aforementioned valves 12 (and valves 112, 212 described below). The valve 612 is adhered to the bag 100. The bag 100 has an internal surface 104 and an external surface 102. The extended flange 210 is adhered to the bag 100 on the internal surface 104. The plunger 62 also has at least two openings, a first opening 64 and a second opening 66. A channel 68 is located within the interior of the plunger and connects the first opening 64 and the second openings 66, thereby forming a fluid pathway to a downstream component. The first opening 64 is located in the first portion 24 of the plunger, and the second opening 66 is located in the second portion 25 of the plunger. In some embodiments, the plunger 62 can contain additional openings and interior fluid pathways. As shown, when the valve 612 is in the closed position the bottom end 63 of the plunger is in alignment with the flange 210, forming a face 90, and providing the valve with a steam-able surface and a sterile barrier against the environment for the interior of the valve, plunger and any downstream components. It is to be noted that the face 90, the extended flange 210, as well as the internal surface 104 of the bag 100, are substantially coplanar and, accordingly, a no dead-leg condition is created. In some embodiments, the surface of the plunger is higher than a top surface of the flange while in a closed position, wherein a sealed condition is maintained by an o-ring. As shown, the plunger 62 is attached to tubing 202, downstream of the bag 100.

Figure 6:
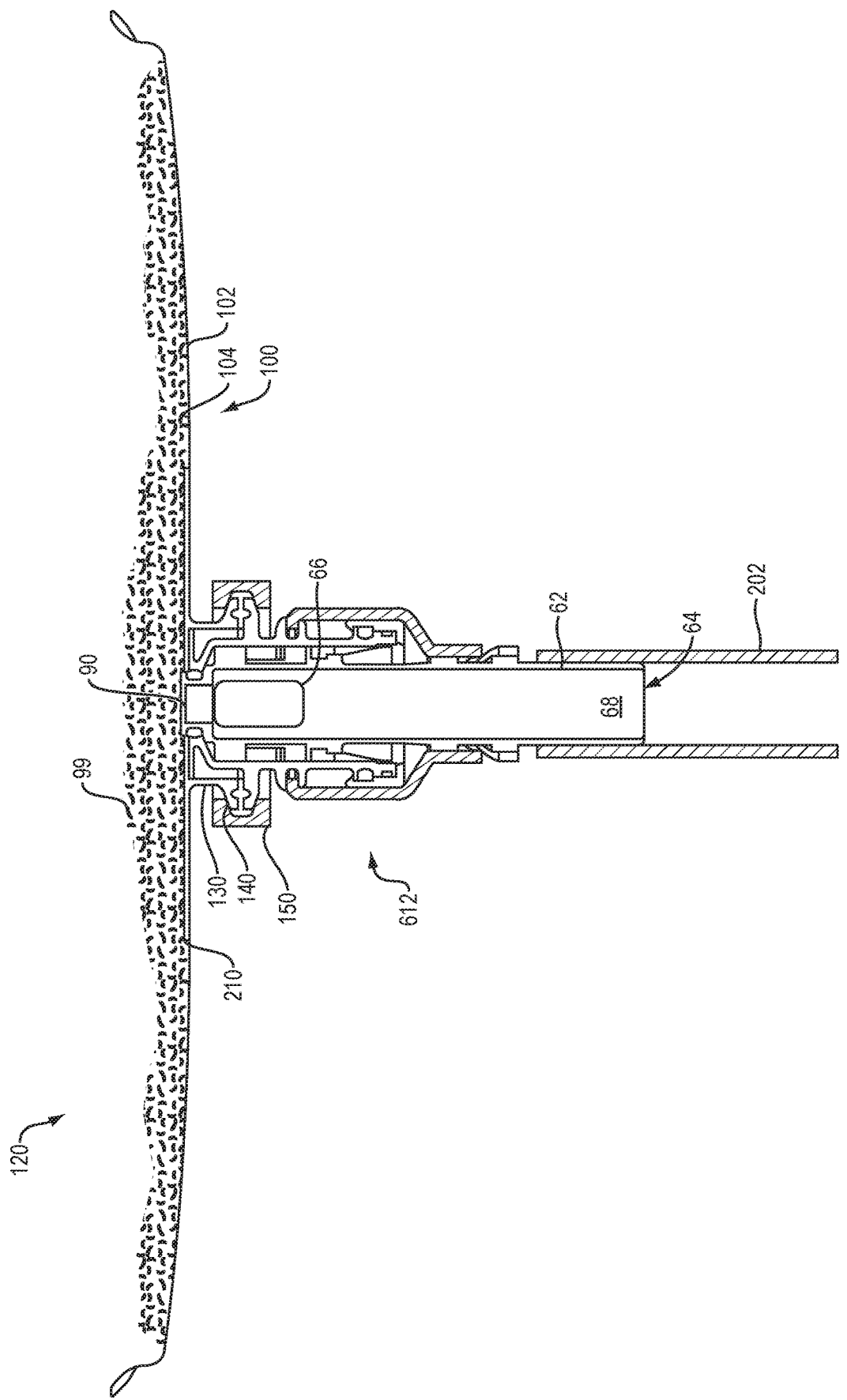
FIG. 6 is a cross-sectional front view of FIG. 5 of a valve having an extended flange adhered to a bag or biocontainer, further depicting a solid processing aid, according to embodiments of the disclosure.

FIG. 6 is a cross-sectional view of FIG. 5 of a valve 612 having an extended flange 210 adhered to a bag or biocontainer 100, further depicting a solid processing aid 99, according to embodiments of the disclosure. As shown, the processing aid 99 is inside the bag 100. The valve 612 is closed and all of the processing aid 99 is clearly available for dissolving. Accordingly, there is no dead-leg region. In other words, all of the processing aid 99 is similarly situated within the bag 100. And, there is no area within the bag 100 that would be expected to have any different physical property (such as a concentration difference within a liquid solution within the bag 100). It can be furthered termed that of the systems (the bag 100) and valves (12, 112, 212, 612) described herein have a "negative" dead leg. Because the face 90 of the plunger 62, when in a closed position, actually protrudes or projects above the internal surface 104 of the bag 100 and/or the extended flange 80a, 80b, 80c, 110, 210 and the like, there can be no dead leg for a processing aid or a stagnant area to form within the hag 100.

Figure 7:
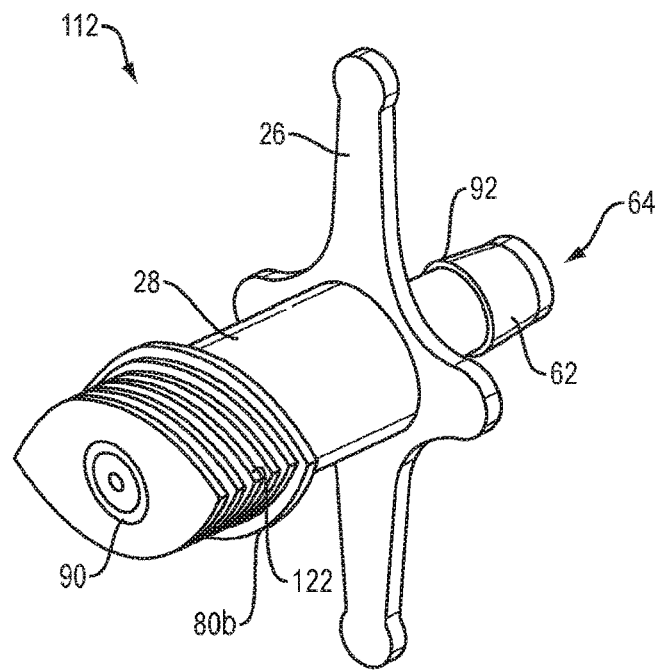
FIG. 7 is a perspective view of a second embodiment of a valve for use with a two-dimensional bag, according to embodiments of the disclosure.

FIG. 7 is a perspective view of a second embodiment of a valve 112 for use with a two-dimensional bag (not shown), according to the disclosure. The valve 112 comprises a first opening 64 adjacent a plunger 62. The plunger 62 comprises a barb termination 92 for connecting the valve to a downstream component on a first end. The valve 112 further comprises a first flange 80b having an attachment region 122. The attachment region 122 is capable of attaching to a 2D bag, bioreactor, or container (not shown). The attachment region 122 may be adhered to a bag via, for e.g., an adhesive and/or heat-sealing. A face 90 of the plunger 62 (while in a closed position) also extends into a closed volume of a 2D bag (not shown). When using valve 112 to fill a downstream component such as a collection vessel, the valve 112 is opened by rotating the first section 26, which moves the plunger 62 linearly away from the face 90, permitting fluid to enter opening and to eventually flow out the opening 64. Once a bag or bioreactor is full, the first section 26 is rotated in the opposite direction to move the plunger linearly again, this time in the opposite direction, in order to seal the opening closed to the fluid from an upstream component. In practice, where the attachment region 122 is adhered to the bag, the second section 28 is held stationary and the first section 26 is rotated, so as to not stress the adhesion between the attachment region 122 and the bag or bioreactor 100. Flats, as described above, may be disposed or molded into the second section 28 for ease of gripping.

Figure 8:
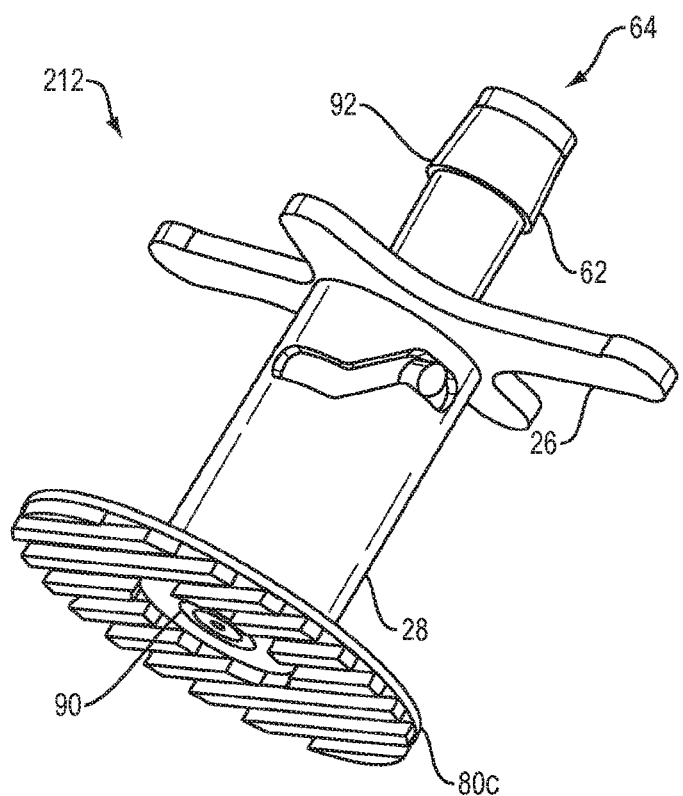
FIG. 8 is a perspective view of a third embodiment of a valve for use with a two-dimensional bag, according to embodiments of the disclosure.

FIG. 8 is a perspective view of a third embodiment of a valve 212 for use with a two-dimensional bag, according to embodiments of the disclosure. A valve 212 comprises a first opening 64 adjacent a plunger 62. The plunger 62 comprises a bad) termination 92 for connecting the valve 212 to a downstream component on a first end. The valve 212 further comprises a first flange 80c, which is capable of attaching to a bag, bioreactor, or container (not shown). Flats, as described above, may be disposed or molded into the second section 28.

Figure 9:
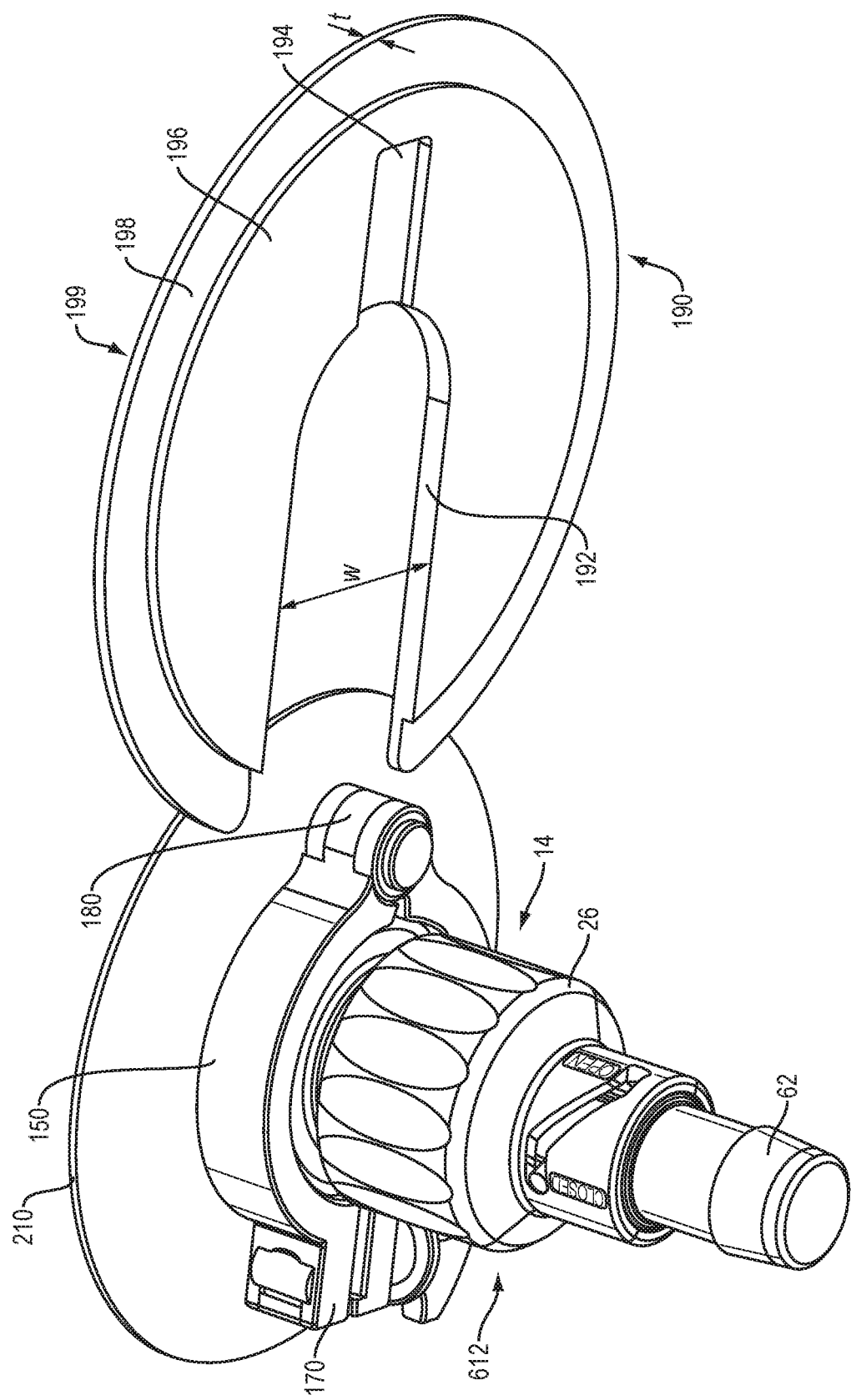
FIG. 9 depicts an extended flange, a valve, and a clamp in an assembled state, such as is depicted in FIG. 4C, further comprising a drain plate in an exploded view, according to embodiments of the disclosure.

FIG. 9 depicts an extended flange 210, a valve 612, and a clamp 150 in an assembled state, such as is depicted in FIG. 4C, further comprising a drain plate 190 in an exploded view, according to embodiments of the disclosure. The drain plate 190 comprises a first plane 199, wherein the first plane 199 would contact the extended flange 210 when assembled, as discussed below. Opposite the first plane 199 is a first surface 198 and a second surface 196, wherein the second surface is distal to the first plane 199 and the first surface 198 is disposed between the first plane 199 and the second surface 196. The second surface 196 comprises a diameter lesser than a diameter of the first surface 198. A through slot 192, having a width w, traverses through at least half of the diameter of drain plate 190. A second slot 194, at a distal end of the through slot 192, traverses through approximately half of a thickness t of the drain plate 190. The width w of the through slot 192 is less than that of the clamp 150.

The drain plate 190 may be disposed below the extended flange 210. The clamp 150 comprises a hinge 180 opposite the clasp 170. Once the clamp, as described above, the tri-clamp 150, is assembled with the valve, as shown the valve 612, the clasp 170 may then be tightened, forming a liquid tight seal. In practice, the extended flange 210 may first be adhered to a bag or container (shown below) and subsequently assembled to the recessed flange as discussed above. Once the valve 612 is assembled, it can be operated. As shown, the valve 612 is in a closed position. The hinge 180 slides into the second slot 194. At least part of the second surface 196 is disposed between the extended flange 210 and the clamp 150. The drain plate 190 may be manufactured from any suitable material, e.g., metals, ceramics, plastics, and the like. At least one exemplary material is steel and, in particular, a stainless steel. A drain plate 190 made of stainless steel can easily be washed and re-used.

To open the valve 612, a user need not grip the clamp 150. In contrast, a user can, with one hand, rotate the first section 26 of the body 14. Rotating the body 14 of the valve 612, while non-rotating the clamp 150 allows a user to open the valve 612 without compromising the seal between the bag and the extended flange 210 and without gripping the clamp 150. Furthermore, because of the interference between clamp 150, the drain plate 190, and the extended flange 210, no rotational force is transmitted to the extended flange 210, and therefore no risk of damaging the seal between the bag (not shown) and the extended flange 210 is possible.

Because the fluid transfer device or valve 12, 112, 212, 612, 1112 is preferably provided in a sterile condition, (i.e., the interior of the system and any component connected downstream of the valve is pre-sterilized such as with gamma radiation, ethylene gas or the like and shipped in a sterile condition), some type of use indicator (not shown) may be helpful, and capable of informing a user when a system has been used. As an alternative, or in addition to any of the indicator mechanisms discussed above, a shrink wrap indicator (not shown) may be located over the valve or at least over the rotating first section of the device to indicate whether the valve had been used.

The valve 12, 112, 212, 612, 1112 may comprise a plastic material and may be formed by machining the body and plunger assemblies and then applying the necessary seals and the like or, in some embodiments, by molding the body and the plunger separately and assembling them with seals and other components. Alternatively, the body may be molded into two separate halves, e.g., longitudinal halves, and assembled by attaching the plunger component with seals and other components to one half of the body, followed by the attaching the remaining half of the body to the plunger, seals, other components, and the first half of the body.

The valve 12, 112, 212, 612, 1112 may be made of a metal and/or any plastic material capable of withstanding steam sterilization. The temperature and pressure of such sterilization is typically approximately 121° C. and 1 bar above atmospheric pressure. In some instances, harsher conditions, such as 142° C. and up to 3 bar above atmospheric pressure, may be employed. The body and at least the face of the plunger may be capable of withstanding these conditions. In some embodiments, the valve 12, 112, 212, 612, 1112 is made of the same material and is capable of withstanding these conditions. Suitable materials for this valve include but are not limited to PEI (polyetherimide), polyether-ether ketone (PEEK), polyether ketone (PEK), polysulphones, polyarylsulphones, polyalkoxysulphones, polyethersulphones, polyphenyleneoxide, polyphenylenesulphide, polytetrafluoroethylene (PTFE), and/or blends thereof. Alternatively, one can make the face portion from ceramic or metal inserts alone, or that are overmolded with a plastic cover. One can also form a polymeric face with a metal outer layer using plasma coating processes.

Figure 10:
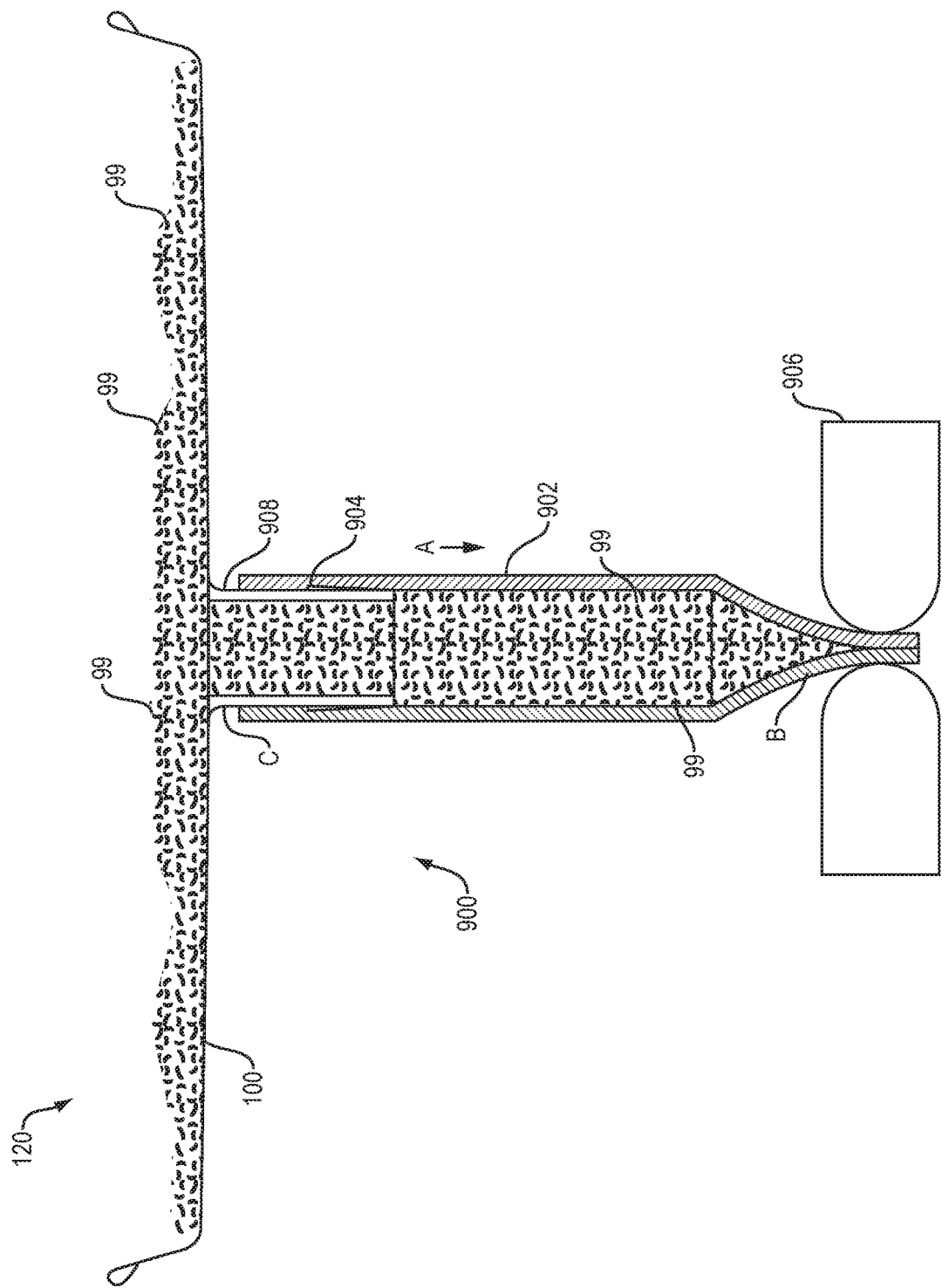
FIG. 10 is a prior art system comprising a bag having a port, tube clamp, and a dead leg tube region.

The foregoing embodiments of the disclosure solves the dead-leg problem of the prior art, see, for example, FIG. 10. FIG. 10 is a prior art system 900 comprising a hag 100 having a port 908, a tube clamp 906, and a tube 902 (in cross section), whereby a dead leg region is created. The prior art system 900 was/is used for mixing, sampling and/or delivering a biological fluid 120 containing a processing aid 99, such as an adjuvant, from the bag 100. The fluid 120 from the bag 100 (having a closed volume, not shown) flows in direction A from the closed volume into the tube 902. The tube 902 is connected to the bag 100 via a port 908 having a barb connector 904. The tube 902 is pinched off by a tube clamp 906. In some systems, a single use valve (not shown) may be disposed between the port 908 and the tube 902. The fluid 120 can be dispensed out of the system 900 by opening the tube clamp 906. The drawback with this system is that the fluid 120 can flow freely through the port 908 and into the tube 902, wherein a region 910 represents a dead-leg area. As shown, the dead-leg area 910 has the processing aid 99, which have settled from the bag 100 or bioreactor into the dead leg region 910. Any part of the tube 902, from an upper point B to a lower point C represents the dead leg region 910. Any of the processing aid 99 in the dead leg region 910 can no longer be dissolved within the bag 100, i.e., waste. Furthermore, any sample taken from the bag 100 through the dead leg region 910 is unlikely to have a concentration that is representative of the fluid within the bag 100. Furthermore, past attempts at creating a system having no dead leg, regions have failed. For example, moving the clamp 906 closer to the bag 100 does not work. It is not possible to obtain a sufficiently tight seal because the port 908 and the tube 902 overlap. Furthermore, damage to the port 908 and/or the bag 100 results. Having a clamp any lower so that the port 908 and the tube 902 are not overlapped necessarily creates a dead leg region. Further still, the barb connector 904 would be moved from the tube 902 when the clamp 906 is so close in proximity to the port 908 creating areas for leaks.

Figure 11:
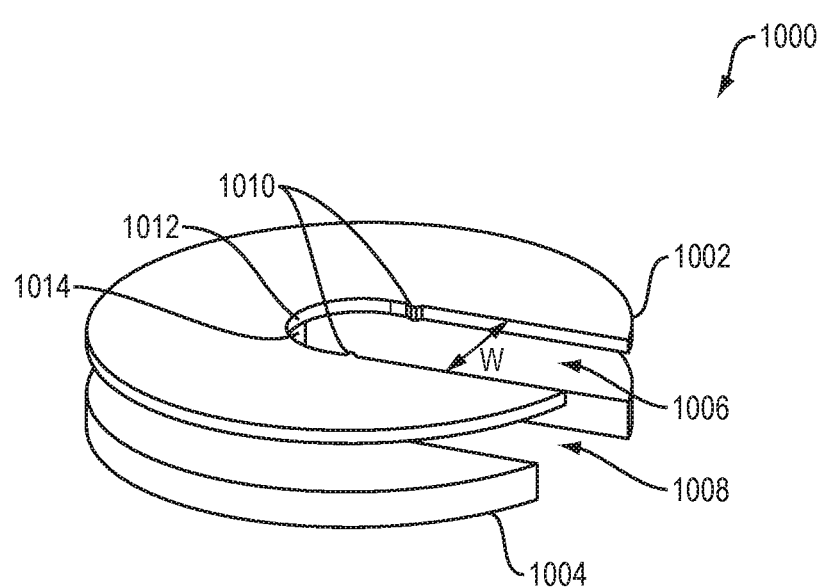
FIG. 11 is a perspective view of an additional embodiment of a locking tool for use with a valve and a bag, according to embodiments of the disclosure.

FIG. 11 is a perspective view of an additional embodiment of a valve for use with a bag, according to embodiments of the disclosure. Some smaller valves, e.g., valves having tubing attached wherein, a tubing diameter is less than approximately 15-30 mm, can be difficult to manipulate manually. Some embodiments may be difficult to manipulate, i.e., open and close, via rotation of parts of the valve. Therefore, some embodiments of the disclosure comprise a valve, wherein the valve is open and closed using a push-pull manipulation.

FIG. 11 is a perspective view of an embodiment of a locking tool 1000 for use with a valve and a bag, according to embodiments of the disclosure. The locking tool 1000 comprise an upper plane 1002 and a lower plane 1004 with a vertical wall 1014 disposed therebetween. The vertical wall 1014 is opposite a lower slot 1008 and an upper slot 1006. The vertical wall 1014 forms a minor arc that connects the upper plane 1002 and the lower plane 1004. The upper slot 1006 comprises a slot width W that is smaller than or the same as a width of the lower slot 1008. The locking tool 1000 optionally comprises a distal circular area 1012. Two ribs 1010 are formed adjacent to the distal circular area 1012. The ribs 1010 may locate and releasably lock a valve (shown below) within the upper slot 1006. A radius of the distal circular area 1012 may be substantially similar to a radius of curvature of a valve placed therein. The locking tool 1000, when having a valve, which is connected to a bag, as described above, disposed therein permits an operator to actuate the valve, as discussed more fully below. The locking tool 1000 may be manufactured from any suitable material, e.g., metals, ceramics, plastics, and the like. At least one exemplary material is steel and, in particular, a stainless steel. A locking tool 1000 made of stainless steel can easily be washed and re-used. Alternatively, a locking tool 1000 made of a plastic may be easy to sterilize and inexpensive, which may be chosen in single-use applications.

Figure 12:
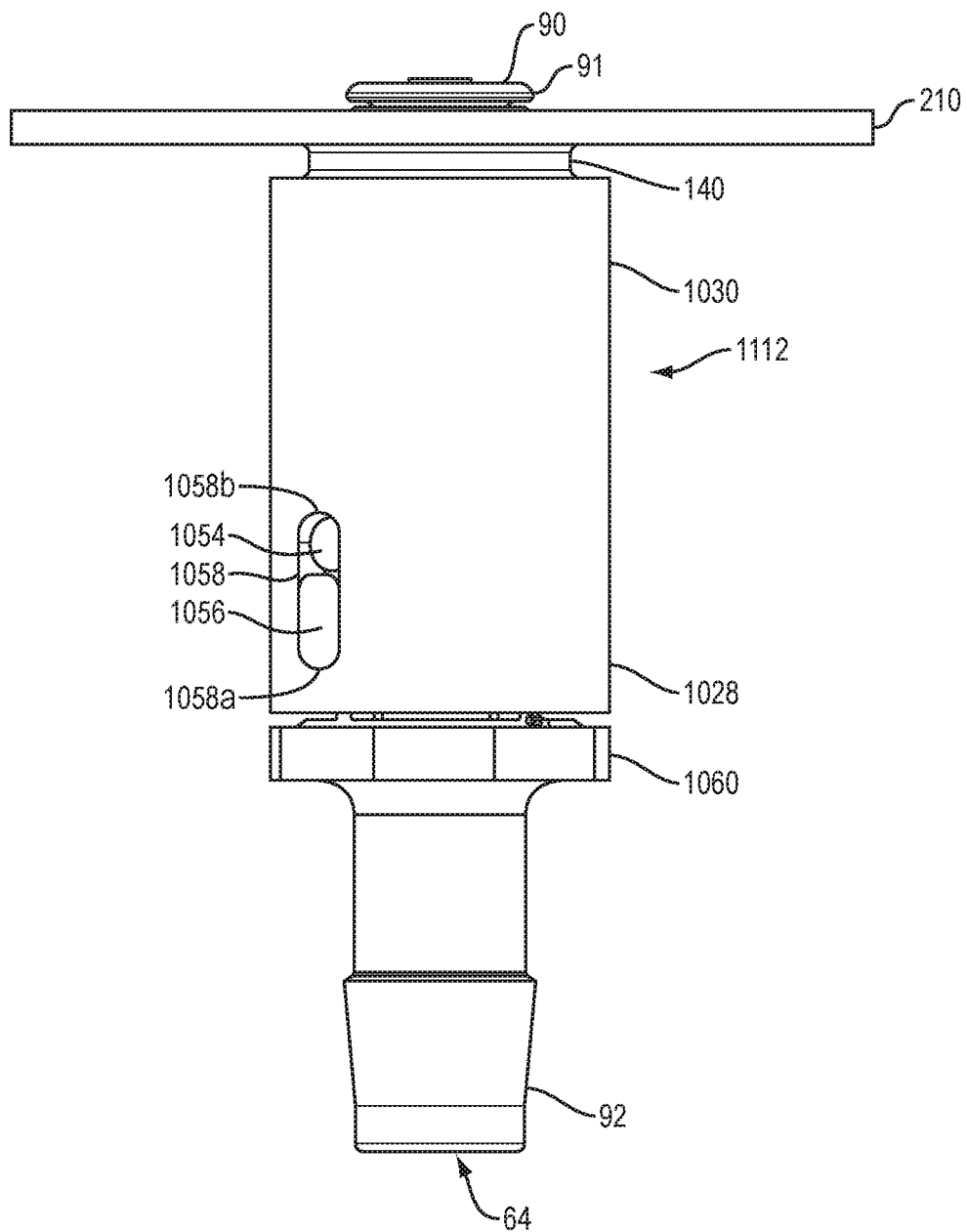
FIG. 12 is a front view of a valve for use with a bag, according to some embodiments of the disclosure.

FIG. 12 is a front view of a valve 1112 for use with a bag, according to some embodiments of the disclosure. The valve 1112 may be actuated with a push-pull manipulation. For example, an operator may hold a conical body section 1028 of the valve 1112 and pull to open the valve 1112 or push to close the valve 1112 by gripping a lower section 1060. However, there is no need for an operator to hold the body section 1028 while pulling and/or pushing the valve 1112. The operator may simply pull or push the lower section 1060. The locking tool 1000 supports the valve 1112 when pulled or pushed. The lower section 1060 has the bore connected therewith, which telescopes within the body section 1028. The body section 1028 may have an operation slot 1058 disposed therein. An upper portion 1030 of the body section 1028 may mate with the locking tool 1000, as shown more fully below. The extended flange 210 further comprises a shoulder 140 for mating with the valve 1112. The operation slot 1058 has a closed end 1058b and an open end 1058a. A pin 1054 is connected to a plunger (not shown) of the valve 1112. The operation slot 1058 restricts the linear and axial movement of the plunger via the pin 1054 from the open end 1058a to the closed end 1058b. The plunger is connected to a face 90 on a distal end of the plunger, wherein the plunger is disposed within the bore, as described above. The plunger may have two or more circumferential seals (not shown), wherein an opening (not shown) leads to a central plunger bore for fluid transfer. A seal, e.g., an o-ring 91 surrounds the face 90, providing a liquid tight seal with a hole in the extended flange 210 when in a closed position, as shown. When the valve 1112 is opened, the face 90 and the o-ring 91 become recessed through the extended flange 210, providing fluid communication between a bag (not shown, but as described above) and a channel or bore through the plunger and a lower section 1060 and an opening 64. A barb fitting 92 for accommodating, for example, tubing, is also shown. A lock 1056 may be placed in the operation slot 1058, for preventing the inadvertent movement of the pin 1054 from a valve closed position 1058b and a valve open position 1058a and vice-versa.

Figure 13:
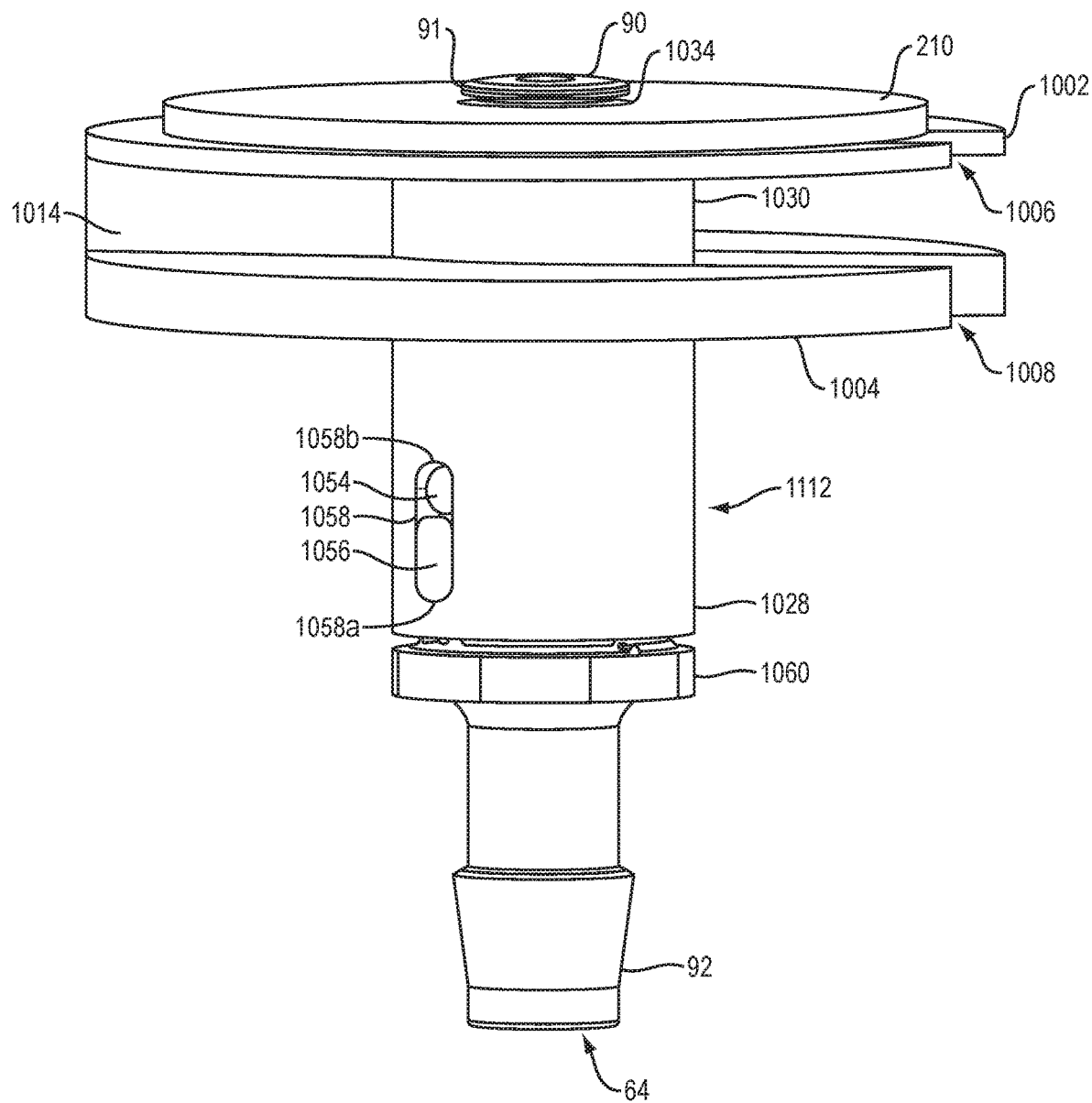
FIG. 13 depicts a perspective view of the valve of FIG. 12 disposed within the locking tool of FIG. 11, for a fluid transfer system, according to embodiments of the disclosure.

FIG. 13 depicts a perspective view of the valve of FIG. 12 disposed within the locking tool of FIG. 11, for a fluid transfer system, according to embodiments of the disclosure. A zero dead-leg fluid transfer system, comprises a valve, comprising a conical body section having a lower body section and an upper body section, wherein an extended flange is joined to the upper body section; and a plunger having a central bore that disposed within the conical upper body section, wherein the plunger comprises at least one seal adjacent a face, wherein the valve is open and closed via a pull/push manipulation that causes the plunger to become longitudinally displaceable within the conical body section; and a locking tool, wherein the locking tool comprises an upper plane and a lower plane having a vertical wall disposed therebetween, further comprising a vertical wall opposite a lower slot and an upper slot, wherein the conical body section of the valve is situated within at least one of the lower slot or the upper slot, and wherein the at least one seal on the plunger forms a fluid tight seal between the plunger and the extended flange.

A fluid transfer device, e.g., a valve 1112 having a body section 1028 having an elongate bore (not shown) formed through at least a portion of the lower section 1060, e.g., a generally hollow moveable plunger, i.e., a longitudinally displaced plunger, contained within the elongate bore, as described above. The plunger moves axially and linearly with respect to the body section 1028. The plunger inside the valve 1112 is driven linearly (e.g., axially), thereby operating (i.e., opening and closing) the valve 1112. The face 90 is drawn into the valve 1112 when in an open position (as shown, the valve is in a closed position). The extended flange 210 is attached to a surface of a bag (not shown in FIG. 13, substantially as described above), e.g., either an outer surface of the bag or an internal surface of the bag. An operator can place the locking tool 1000 around the upper portion 1030 of the body section 1028 and securely pull on the lower section 1060 of the valve 1112 to open the valve 1112 without tearing the bag. The operator may place a hand under the locking tool 1000 when pulling with another hand on the lower portion 1060. As above, however, only one hand is needed, whether pulling or pushing lower portion 1060. Similarly, an operator can grip the locking tool 1000 and push the lower portion 1060 to close the valve 1112 without risk to the integrity of the bag. The extended flange 210 is attached to the body section 1028 adjacent the upper portion 1030. The extended flange 210 attaches to the bag, has a hole 1034 therethrough so that the face 90 and the o-ring 91 on the face 90 of the plunger can become recessed and allowing fluid communication with the hollow plunger and forms a liquid tight seal therewith. In some embodiments, a tube, such as a tube having an internal diameter of 10-25 mm or smaller, is attached to the barb fitting 92.

Embodiments according to the disclosure also include methods for processing biological fluids. For example, a biological fluid(s) can be delivered or otherwise provided within a bag or bioreactor having an inner volume. A fluid transfer device, such as a valve is in downstream fluid communication with the bag or bioreactor. Generally, a downstream component, such as a valve, is located near or at a bottom of the bag or bioreactor. The fluid transfer device is attached to the bag or bioreactor along an extended area of a flange that is attached to or an integral part of the fluid transfer device. The biological fluids are mixed. Typical means for mixing the biological fluids comprise an impeller and/or mixing blade. The impeller may be attached to a physical shaft as a drive mechanism. Alternatively, the impeller may be powered by a magnetic drive pump, using a balanced magnetic field to create the rotation of the impeller. During rotation, the rotating magnetic field affects the inner impeller magnet. As the two magnets begin to turn together, the impeller begins turning and, therefore, displacing fluid. In addition, a solid processing agent may be delivered to the inner volume. The solid processing agent is mixed with the biological fluids. In some embodiments, the fluid transfer device comprises a flange. The flange may comprise a relatively large surface for attachment to the bag or bioreactor. Also, the fluid transfer device may comprise a plunger for providing a fluid tight seal when in a closed position and for allowing delivery of fluids when in an open position. In some embodiments, the flange comprises a top surface that is substantially coplanar with a surface of the plunger during a closed position. In some embodiments, the surface of the plunger is higher than a top surface of the flange. Because the flange is adhered to the bag or bioreactor, the mixing is performed absent a dead-leg region, vastly increasing mixing efficiency. Furthermore, if, for example, a sample is needed during the processing of fluids, the sample will also be more representative of concentrations of various agents and aids. For example, one difficult to mix agent is an aluminum salt, typically used as an adjuvant. In some embodiments, the method includes a biological fluid for culturing, e.g., monoclonal antibodies.

In accordance with certain embodiments, the bag, bioreactor, or single use container is designed to receive and maintain a fluid. In some embodiments, the bag, bioreactor, or single use container comprises monolayer walls or multilayer flexible walls formed of a polymeric composition such as polyethylene, including ultrahigh molecular weight polyethylene (UHMWPE), ultralow density polyethylene (ULDPE), linear low density polyethylene (LLDPE), low density polyethylene (LDPE), medium density polyethylene (MDPE); polypropylene (PP); ethylene vinyl alcohol (EVOH); polyvinyl chloride (PVC); polyvinyl acetate (PVA); ethylene vinyl acetate copolymers (EVA copolymers); thermoplastic elastomers (TPE), and/or blends or alloys of any of the foregoing materials as well as other various thermoplastics materials and additives as are known to those in the art. The single use container may be formed by various processes including, but not limited to, co-extrusion of similar or different thermoplastics; multilayered laminates of different thermoplastics; welding and/or heat treatments, heat staking, calendaring, or the like. Any of the foregoing processes may further comprise layers of adhesives, tie layers, primers, surface treatments, and/or the like to promote adhesion between adjacent layers. By "different," it is meant different polymer types such as polyethylene layers with one or more layers of EVOH as well as the same polymer type but of different characteristics such as molecular weight, linear or branched polymer, fillers and the like, are contemplated herein. Typically, medical grade plastics and, in some embodiments, animal-free plastics are used to manufacture the containers. Medical grade plastics may be sterilized, for e.g., by steam, ethylene oxide or radiation, including beta and/or gamma radiation. Also, most medical grade plastics are specified for good tensile strength and low gas transfer. In some embodiments, the medical grade plastics comprise a polymeric material that is clear or translucent, allowing visual monitoring of the contents and, typically, are weldable and unsupported. In some embodiments, the container may be a bioreactor capable of supporting a biologically active environment, such as one capable of growing cells in the context of cell cultures. In some embodiments, the bag, bioreactor or container may be a two-dimensional (2D) or "pillow" bag or, alternatively, the container may be a three-dimensional (3D) bag. The particular geometry of the container or bioreactor is not limited in any embodiment disclosed herein. In some embodiments, the container may include a rigid base, which provides access points such as ports or vents. Any container described herein may comprise one or more inlets, one or more outlets and, optionally, other features such as sterile gas vents, spargers, and ports for the sensing of the liquid within the container for parameters such as conductivity, pH, temperature, dissolved gases, e.g., oxygen and carbon dioxide, and the like as known to those in the art. The container is of a sufficient size to contain fluid, such as cells and a culture medium, to be mixed from bench-top scale to, e.g., 3000 L or larger bioreactors.

The inner wall of the plastic film may be specified to heat bond with the flange of the fluid transfer device, e.g., valve. Similarly, where a specific plastic film is indicated, the flange, generally comprising a polymeric material, may be specified to heat bond with the specific plastic film. In some embodiments, a bond may be created between the flange and the plastic film using ultrasonic welding, RF welding, contact heating, inductive heating, and other heating methods known to those in the art. In some embodiments, a primer between the plastic film and the flange may be used. In some embodiments, an adhesive tie layer is used to bond the plastic film and the flange. The flange may be of any suitable thickness. The thickness of the flange, in some embodiments, is a function of the stiffness desired. For example, the flange comprising a polypropylene polymeric material, may be from approximately, for e.g., 1.0 to 3.0 millimeters in thickness. In some embodiments of the disclosure, the flange may comprise a surface treatment so that bonding with the plastic film is enhanced, for example, an ozone treatment. In some embodiments, the flange is steam and/or gamma radiation stable for sterilization purposes. In some embodiments, the diameter of the flange may be specified for certain applications. For example, for applications requiring elevated amounts of tough-to-dissolve processing aids, it may behoove the user to use a larger flange so that any initially undissolved material remains in an area within the bioreactor where mixing is most efficient. In some embodiments, the flange may be used as a means for locating/orienting the device. For example, see U.S. Pat. Nos. 9,187,240; 9,272,840; and 9,090,398 as filed by the EMD Millipore Corporation, technologies of which are incorporated by reference in entirety.

Some embodiments of valves in accordance with the disclosure are found in, for example, U.S. Pat. Nos. 8,690,120 and 10,247,312, as filed by the EMD Millipore Corporation, each of which is incorporated by reference in its entirety.

In some embodiments, the bag, bioreactor, or container may be a single use, deformable, foldable bag that defines a closed volume, is sterilizable for single use, capable of accommodating contents, such as biopharmaceutical fluids, in a fluid state, and can accommodate a mixing device partially or completely within the closed volume of the container, e.g., working volume. In some embodiments, the closed volume can be opened, such as by suitable valving, to introduce a fluid into the volume, and to expel fluid therefrom, such as after mixing is complete.

In some embodiments, each container contains, either partially or completely within its interior, an impeller assembly for mixing, dispersing, homogenizing, and/or circulating one or more liquids, gases and/or solids contained in the container. The impeller assembly may include one or more blades, which are movable, such as by rotation or oscillation about an axis. The impeller assembly converts rotational motion into a force that mixes the fluids it contacts. The impeller assembly may be formed in the top of the container and via a shaft extend downward into the container volume. The shaft is connected to a motor outside of the container and the shaft has one or more impeller blades on it. Such assemblies often being referred to as "lightning-style" assemblies. Also, in some embodiments, the impeller assembly can be formed in a bottom portion of the container and is connected to a motor by a direct shaft to a motor outside the container or, alternatively, is magnetically coupled to the motor so no shaft needs to penetrate through the container wall.

All ranges for formulations recited herein include ranges therebetween and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4, or 3.1 or more.

Reference throughout this specification to "one embodiment," "certain embodiments," "one or more embodiments," "some embodiments," or "an embodiment" indicates that a feature, structure, material, or characteristic described in connection with the embodiment is included in at least one embodiment of the disclosure. Therefore, the appearances of the phrases such as "in one or more embodiments," "in certain embodiments," "in one embodiment," "some embodiments," or "in an embodiment" throughout this specification are not necessarily referring to the same embodiment.

Although some embodiments have been discussed above, other implementations and applications are also within the scope of the following claims. Although the specification describes, with reference to particular embodiments, it is to be understood that these embodiments are merely illustrative of the principles and applications of the present disclosure. It is therefore to be further understood that numerous modifications may be made to the illustrative embodiments and that other arrangements and patterns may be devised without departing from the spirit and scope of the embodiments according to the disclosure. Furthermore, particular features, structures, materials, or characteristics may be combined in any suitable manner in any one or more of the embodiments.

Publications of patent applications and patents and other non-patent references, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A valve comprising:
    a body having a first section and a second section;
    an elongate bore extending through the body and having a proximal end and a distal end;
    a longitudinally displaceable plunger disposed in and extending along the bore, the plunger having a proximal end and a distal end and having a first position displaced toward the distal end of the bore and a second position displaced toward the proximal end of the bore, the plunger further comprising a top surface;
    a diaphragm seal attached to the proximal end of the plunger and sealing the bore at the proximal end thereof;
    a gland seal sealing the bore at a location intermediate the diaphragm seal and the distal end of the bore;
    the plunger extending through and being sealingly secured to the gland seal;
    a flange attached to the second section of the body or disposed as an integral part of the second section of the body, wherein a top surface of the flange is substantially coplanar with the top surface of the plunger or wherein the top surface of the plunger is higher than a top surface of the flange, and wherein the flange is configured to form a bond with an interior surface of a flexible bioreactor bag;
    a fluid transfer opening in the bore between the diaphragm seal and the gland seal;
    longitudinal displacement of the plunger moving the diaphragm seal to open the bore, the gland seal stretching to accommodate the displacement of and maintain a seal about the plunger, a fluid flow path being established between the open proximal end of the bore and the fluid transfer opening, wherein longitudinal displacement of the plunger towards its first position moves the diaphragm to open the bore.

2. The valve of claim 1, wherein a surface of the flange is approximately coplanar with a surface of the second position when the plunger is displaced toward the proximal end of the bore, creating a zero dead leg position.

3. The valve of claim 1, wherein the portion of the bore between the diaphragm seal and the gland seal is substantially aseptic.

4. The valve of claim 3, further comprising a substantially aseptic connecting component for attaching the valve to an upstream component.

5. The valve of claim 1, wherein the diaphragm seal is disposed at least partially inside the proximal end of the bore prior to displacement of the plunger.

6. The valve of claim 1, wherein the gland seal and/or diaphragm seal is constructed of a silicone elastomer or a solvent resistant fluoroelastomer.

7. The valve of claim 1, wherein the body comprises a substantially cylindrical outer portion, at least one alignment slot for the plunger, and a groove for the gland seal.

8. The valve of claim 1, wherein the flange forms a heat-sealed bond or an adhesive bond with the flexible bioreactor bag.

9. A valve comprising:
a body;
an elongate bore extending through the body and having a proximal end and a distal end;
a longitudinally displaceable plunger disposed in and extending along the bore, the plunger having a proximal end and a distal end and having a first position displaced toward the distal end of the bore and a second position displaced toward the proximal end of the bore;
at least one seal mounted on the plunger to form a fluid tight seal between the plunger and the bore; and
a fluid transfer opening in the plunger between the proximal end of the plunger and the distal end of the plunger; and
a flange coupled to the body, the flange having a top surface and bottom surface opposite the bottom surface, wherein the bottom surface of the flange is configured to be coupled to an interior surface of a flexible bioreactor bag, and
wherein longitudinal displacement of the plunger opening the bore to form a fluid pathway from an upstream component to a downstream component through the fluid transfer opening and a channel within the plunger.

10. The valve of claim 9, wherein the at least one seal is a diaphragm seal.

11. The valve of claim 9, wherein the diaphragm seal is attached to the proximal end of the plunger and seals the bore at the proximal end thereof.

12. The valve of claim 11, wherein the valve further comprises at least one gland seal.

13. The valve of claim 12, wherein the gland seal seals the bore at a location intermediate the diaphragm seal and the distal end of the bore.

14. The valve of claim 12, wherein the plunger extends through and is sealingly secured to the at least one gland seal.

15. The valve of claim 14, wherein the portion of the bore between the diaphragm seal and the at least one gland seal is substantially aseptic.

16. The valve of claim 12, wherein the at least one gland seal stretches to accommodate the displacement of and maintain a seal about the plunger.

17. The valve of claim 11, wherein longitudinal displacement of the plunger towards its first position moves the diaphragm to open the bore.

18. The valve of claim 9, wherein the at least one seal is a gland seal.

19. The valve of claim 9, wherein the body includes a first section and a second section, and the flange being removably coupled to the second section of the body.

20. The valve of claim 9, wherein the body includes a first section and a second section, and the flange being integrally formed with the second section of the body.

21. A zero dead-leg fluid transfer system, comprising:
a valve, comprising:
a conical body section having a lower body section and an upper body section, wherein an extended flange is joined to the upper body section; and
a plunger having a central bore that disposed within the conical upper body section, wherein the plunger comprises at least one seal adjacent a face, wherein the valve is open and closed via a pull/push manipulation that causes the plunger to become longitudinally displaceable within the conical body section; and
a locking tool, wherein the locking tool comprises an upper plane and a lower plane having a vertical wall disposed therebetween, further comprising a vertical wall opposite a lower slot and an upper slot, wherein the conical body section of the valve is situated within at least one of the lower slot or the upper slot, and
wherein the at least one seal on the plunger forms a fluid tight seal between the plunger and the extended flange.

22. The fluid transfer system of claim 21, wherein the at least one seal is a diaphragm seal.

23. The fluid transfer system of claim 21, wherein the diaphragm seal is attached to the proximal end of the plunger and seals the bore at the proximal end thereof.

24. The fluid transfer system of claim 21, wherein the at least one seal is constructed of a silicone elastomer or a solvent resistant fluoroelastomer.

25. The fluid transfer system of claim 21, wherein the extended flange is attached to a bag.

26. The fluid transfer system of claim 21, wherein the plunger comprises a pin.

27. The fluid transfer system of claim 26, wherein the body section comprises an operation slot for housing the pin, wherein the pin restricts the movement of the plunger.

* * * * *